(12) United States Patent
Planz

(10) Patent No.: US 12,350,244 B2
(45) Date of Patent: Jul. 8, 2025

(54) MEK-INHIBITOR FOR THE TREATMENT OF VIRAL AND BACTERIAL INFECTIONS

(71) Applicant: Atriva Therapeutics GmbH, Tübingen (DE)

(72) Inventor: Oliver Planz, Dettingen an der Erms (DE)

(73) Assignee: Atriva Therapeutics GmbH, Tübingen (DE)

( * ) Notice: Subject to any disclaimer, the term of this patent is extended or adjusted under 35 U.S.C. 154(b) by 810 days.

(21) Appl. No.: 17/604,355

(22) PCT Filed: Apr. 16, 2020

(86) PCT No.: PCT/EP2020/060692
§ 371 (c)(1),
(2) Date: Oct. 15, 2021

(87) PCT Pub. No.: WO2020/212478
PCT Pub. Date: Oct. 22, 2020

(65) Prior Publication Data
US 2022/0193017 A1 Jun. 23, 2022

(30) Foreign Application Priority Data
Apr. 16, 2019 (LU) .................... 101183

(51) Int. Cl.
| | | |
|---|---|---|
| *A61P 31/04* | (2006.01) | |
| *A61K 31/196* | (2006.01) | |
| *A61K 31/215* | (2006.01) | |
| *A61K 31/351* | (2006.01) | |
| *A61K 45/06* | (2006.01) | |
| *A61P 31/14* | (2006.01) | |
| *A61P 31/16* | (2006.01) | |

(52) U.S. Cl.
CPC .......... *A61K 31/196* (2013.01); *A61K 31/215* (2013.01); *A61K 31/351* (2013.01); *A61P 31/16* (2018.01)

(58) Field of Classification Search
CPC .......... A61P 31/04; A61P 31/14; A61P 31/16; A61K 31/196; A61K 31/215; A61K 31/351; A61K 45/06; A61K 2300/00; C07C 229/58
See application file for complete search history.

(56) References Cited

U.S. PATENT DOCUMENTS

| | | | | |
|---|---|---|---|---|
| 11,903,917 | B2 * | 2/2024 | Ludwig | .................... A61P 31/12 |
| 2003/0060469 | A1 | 3/2003 | Ludwig et al. | |
| 2022/0370384 | A1 * | 11/2022 | Planz | .................... A61K 31/53 |
| 2022/0378730 | A1 * | 12/2022 | Planz | .................... A61K 31/352 |
| 2023/0241014 | A1 * | 8/2023 | Ludwig | .............. A61K 31/4523 |
| | | | | 514/567 |
| 2024/0245637 | A1 * | 7/2024 | Ludwig | .................... A61P 31/12 |

FOREIGN PATENT DOCUMENTS

| | | |
|---|---|---|
| WO | 2014/056894 A1 | 4/2014 |
| WO | 2015/173788 A1 | 11/2015 |

OTHER PUBLICATIONS

Bright et al., "Adamantane Resistance Among Influenza A Viruses Isolated Early During the 2005-2006 Influenza Season in the United States," The Journal of the American Medical Association (JAMA), vol. 295, No. 8, Feb. 2006, pp. 891-894.
Bruchhagen et al., "Metabolic conversion of CI-1040 turns a cellular MEK-inhibitor into an antibacterial compound," Scientific Reports, vol. 8, No. 1, Jun. 2018, Article No. 9114 (11 pp.).
Carrat et al., "Time Lines of Infection and Disease in Human Influenza: A Review of Volunteer Challenge Studies," American Journal of Epidemiology, vol. 167, No. 7, Jan. 2008, pp. 775-785.
Chertow et al., "Bacterial Coinfection in Influenza—A Grand Rounds Review," The Journal of the American Medical Association (JAMA), vol. 309, No. 3, Jan. 2013, pp. 275-282.
DeClercq et al., "Avian influenza A (H5N1) infection: targets and strategies for chemotherapeutic intervention," Trends in Pharmacological Sciences, vol. 28, No. 6, May 2007, pp. 280-285.
Gillet et al., "Factors Predicting Mortality in Necrotizing Community-Acquired Pneumonia Caused by *Staphylococcus aureus* Containing Panton-Valentine Leukocidin," Clinical Infectious Diseases, vol. 45, No. 3, Jun. 2007, pp. 315-321.
Grundmann et al., "Emergence and resurgence of methicillin-resistant *Staphylococcus aureus* as a public-health threat," The Lancet, vol. 368, No. 9538, Sep. 2006, pp. 874-885.
Haasbach et al., "The MEK-inhibitor CI-1040 displays a broad anti-influenza virus activity in vitro and provides a prolonged treatment window compared to standard of care in vivo," Antiviral Research, vol. 142, Apr. 2017, pp. 178-184.
Hayden et al., "Emergence and Transmission of Influenza A Viruses Resistant to Amantadine and Rimantadine," Current Topics in Microbiology and Immunology, vol. 176, 1992, pp. 119-130.
Hrincius et al., "CRK adaptor protein expression is required for efficient replication of avian influenza A viruses and controls JNK-mediated apoptotic responses," Cellular Microbiology, vol. 12, No. 6, Feb. 2010, pp. 831-843.
Iwao et al., "The emerging ST8 methicillin-resistant *Staphylococcus aureus* cline in the community in Japan: associated infections, genetic diversity, and comparative genomics," Journal of Infection and Chemotherapy, vol. 18, No. 2, Feb. 2012, pp. 228-240.
Laure et al., "Antiviral efficacy against influenza virus and pharmacokinetic analysis of a novel MEK-inhibitor, ATR-002, in cell culture and in the mouse model," Antiviral Research, vol. 178, Apr. 2020, pp. 1048006.

(Continued)

*Primary Examiner* — Brenda L Coleman
(74) *Attorney, Agent, or Firm* — Michael A. Whittaker

(57) ABSTRACT

The present invention relates to PD-0184264 for use in a method for the treatment of a viral infection or a viral and bacterial coinfection. Also provided are compositions comprising such inhibitors for use in the treatment of a virus infection and the prevention and/or treatment of a bacterial co-infection.

23 Claims, 25 Drawing Sheets

(56) References Cited

OTHER PUBLICATIONS

Laure, M., et al. "PD0184264, an active metabolite of the MEK-inhibitor CI-1040 shows superior pharmacokinetics and antiviral activity against influenza virus," 6th International Influenza Meeting, University of Muenster, Germany, Sep. 2018, pp. P112 (2 pp).
LoRusso et al., "Phase I and Pharmacodynamic Study of the Oral MEK Inhibitor CI-1040 in Patients With Advanced Malignancies," Journal of Clinical Oncology, vol. 23, No. 23, Aug. 2005, pp. 5281-5293.
Ludwig, S., "Targeting cell signalling pathways to fight the flu: towards a paradigm change in anti-influenza therapy," Journal of Antimicrobial Chemotherapy, vol. 65, No. 1, May 2009, pp. 1-4.
Mackey et al., "Lessons from SARS and H1N1/A: Employing a WHO-WTO forum to promote optimal economic-public health pandemic response," Journal of Public Health Policy, vol. 33, No. 1, Nov. 2011, pp. 119-130.
Matrosovich et al., "New low-viscosity overlay medium for viral plaque assays," Virology Journal, vol. 3, No. 63, Aug. 2006, pp. 7.
Miller et al., "Staphylococcal PknB as the First Prokaryotic Representative of the Proline-Directed Kinases," PLoS ONE, vol. 5, No. 2, Feb. 2010, pp. e9057 (8 pp).
Monto et al., "Response to the 2009 pandemic: Effect on influenza control in wealthy and poor countries," Vaccine, vol. 29, No. 38, Jul. 2011, pp. 6427-6431.
Moran et al., "Methicillin-Resistant *S. aureus* Infections among Patients in the Emergency Department," The New England Journal of Medicine, vol. 355, No. 7, Aug. 2006, pp. 666-674.
Morens et al., "Predominant Role of Bacterial Pneumonia as a Cause of Death in Pandemic Influenza: Implications for Pandemic Influenza Preparedness," The Journal of Infectious Diseases, vol. 198, No. 7, Aug. 2008, pp. 962-970.
Moss et al., "Targeting pandemic influenza: a primer on influenza antivirals and drug resistance," The Journal of Antimicrobial Chemotherapy, vol. 65, No. 6, Apr. 2010, pp. 1086-1093.
Neumann et al., "Emergence and pandemic potential of swine-origin H1N1 influenza virus," Nature, vol. 459, Jun. 2009, pp. 931-939.
Paddock et al., "Myocardial Injury and Bacterial Pneumonia Contribute to the Pathogenesis of Fatal Influenza B Virus Infection," The Journal of Infectious Diseases, vol. 205, No. 6, Jan. 2012, pp. 895-905.
Parker et al., "Immunopathogenesis of *Staphylococcus aureus* pulmonary infection," Seminars in Immunopathology, vol. 34, No. 2, Oct. 2011, pp. 281-297.
Parry, J., "H7N9 avian flu infects humans for the first time," BMJ, vol. 346, No. I2151, Apr. 2013, pp. 1.
Pinto et al., "Controlling influenza virus replication by inhibiting its proton channel," Molecular BioSystems, vol. 3, Nov. 2006, pp. 18-23.
Pinto et al., "The M2 Proton Channels of Influenza A and B Viruses," The Journal of Biological Chemistry, vol. 281, No. 14, Dec. 2005, pp. 8997-9000.
Pleschka et al., "Influenza virus propagation is impaired by inhibition of the Raf/MEK/ERK signalling cascade," Nature Cell Biology, vol. 3, Feb. 2001, pp. 301-305 and supplementary information, 2 pp.
Rakette et al., "Structural Analysis of *Staphylococcus aureus* Serine/Threonine Kinase PknB," PLoS ONE, vol. 7, No. 6, Jun. 2012, pp. e39136 (9 pp).
Robertson et al., "Prospects for controlling future pandemics of influenza," Virus Research, vol. 162, Nos. 1-2, Dec. 2011, pp. 39-46.
Shilo et al., "Pulmonary Infections and Community Associated Methicillin Resistant *Staphylococcus Aureus*: A Dangerous Mix?" Paediatric Respiratory Review, vol. 12, No. 3, Nov. 2010, pp. 182-189.
Tamber et al., "Role of PknB Kinase in Antibiotic Resistance and Virulence in Community-Acquired Methicillin-Resistant *Staphylococcus aureus* Strain USA300," Infection and Immunity, vol. 78, No. 8, Jun. 2010, pp. 3637-3646.
Taubenberger et al., "Influenza Virus Evolution, Host Adaptation, and Pandemic Formation," Cell Host & Microbe, vol. 7, No. 6, Jun. 2010, pp. 440-451.
Tuchscherr et al., "*Staphylococcus aureus* phenotype switching: an effective bacterial strategy to escape host immune response and establish a chronic infection," EMBO Molecular Medicine, vol. 3, No. 3, Jan. 2011, pp. 129-141.
Wabnitz et al., "In Vitro and in Vivo Metabolism of the Anti-Cancer Agent CI-1040, a MEK Inhibitor, in Rat, Monkey, and Human," Pharmaceutical Research, vol. 21, No. 9, Sep. 2004, pp. 1670-1679.
Gaitonde et al., "Influenza: Diagnosis and Treatment", Am Fam Physician. Dec. 15, 2019;100(12):751-758.
Moscona, Anne, "Neuraminidase inhibitors for influenza", N Engl J Med. Sep. 29, 2005;353(13):1363-73. doi: 10.1056/NEJMra050740.

* cited by examiner

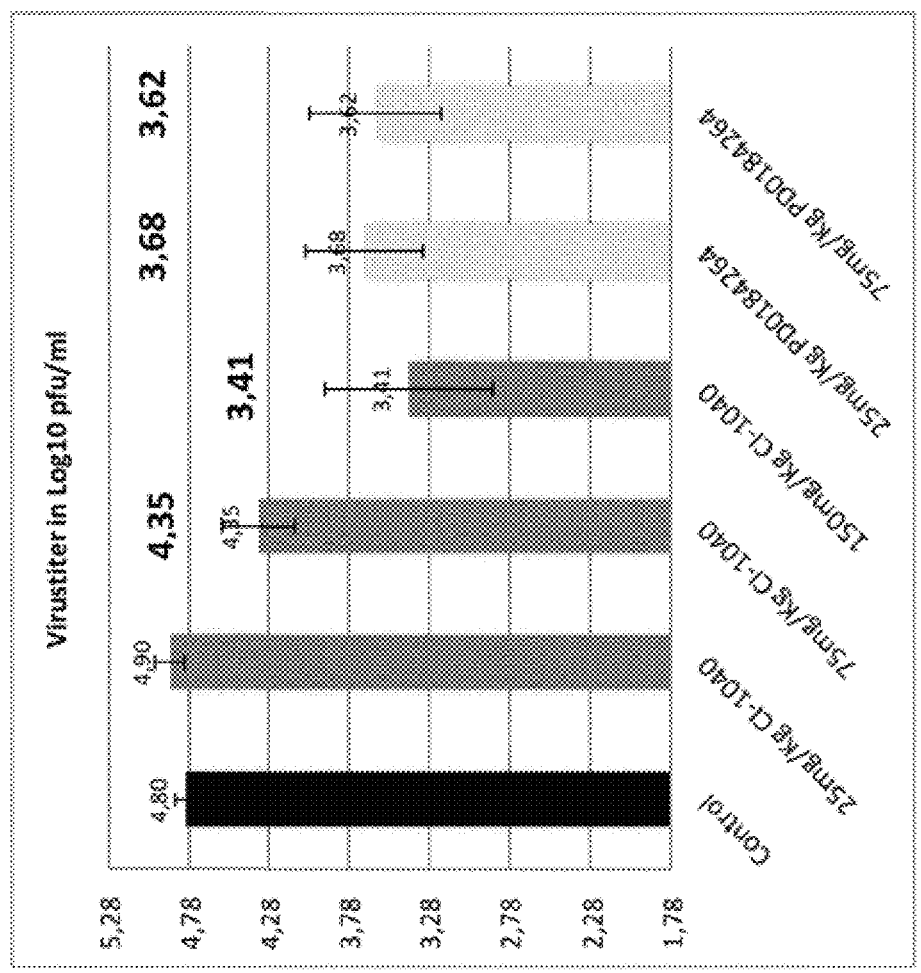

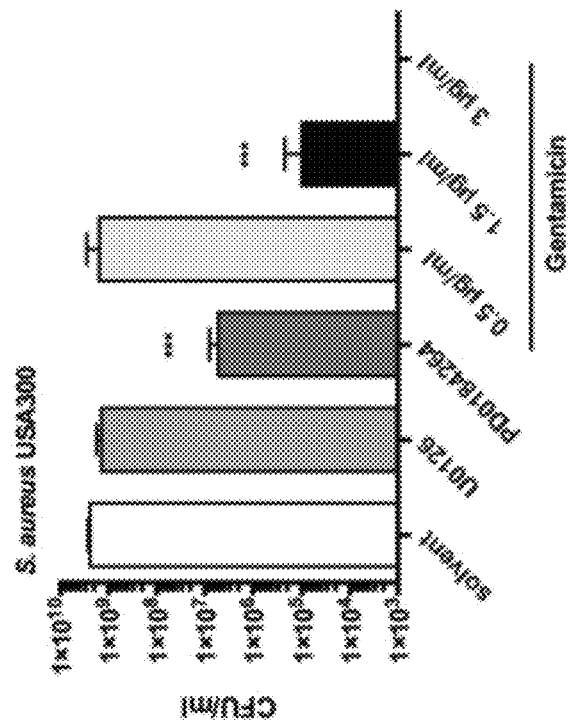
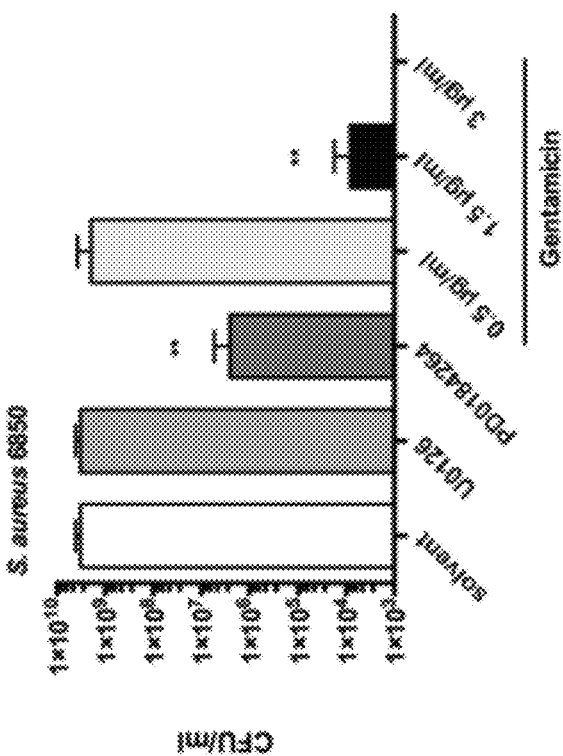
Figure 6

Figure 12 (Table 1)

| Antibiotic class | Generic names |
|---|---|
| Aminoglycosides | Amikacin, Gentamicin, Kanamycin, Neomycin, Netilmicin, Tobramycin, Paromomycin, Spectinomycin |
| Ansamycins | Geldanamycin, Herbimycin, Rifaximin, Streptomycin |
| Carbacephem | Loracarbef |
| Carbapenems | Ertapenem, Doripenem, Imipenem/Cilastatin, Meropenem |
| Cephalosporins (First generation) | Cefadroxil, Cefazolin, Cefalotin or Cefalothin, Cefalexin |
| Cephalosporins (Second generation) | Cefaclor, Cefamandole, Cefoxitin, Cefprozil, Cefuroxime |
| Cephalosporins (Third generation) | Cefixime, Cefdinir, Cefditoren, Cefoperazone, Cefotaxime, Cefpodoxime, Ceftazidime, Ceftibuten, Ceftizoxime, Ceftriaxone |
| Cephalosporins (Fourth generation) | Cefepime |
| Cephalosporins (Fifth generation) | Ceftaroline fosamil, Ceftobiprole |
| Glycopeptides | Teicoplanin, Vancomycin, Telavancin |
| Lincosamides | Clindamycin, Lincomycin |
| Lipopeptide | Daptomycin |
| Macrolides | Azithromycin, Clarithromycin, Dirithromycin, Erythromycin, Roxithromycin, Troleandomycin, Telithromycin, Spiramycin |
| Monobactams | Aztreonam |
| Nitrofurans | Furazolidone, Nitrofurantoin |
| Oxazolidonones | Linezolid, Posizolid, Radezolid, Torezolid |
| Penicillins | Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin |

Figure 12 (cont'/Table 1)

| Penicillin combinations | Amoxicillin/clavulanate, Ampicillin/sulbactam, Piperacillin/tazobactam, Ticarcillin/clavulanate |
|---|---|
| Polypeptides | Bacitracin, Colistin, Polymyxin B |
| Quinolones/ Fluoroquinolone | Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin |
| Sulfonamides | Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic) |
| Tetracyclines | Demeclocycline, Doxycycline, Minocycline, Oxytetracycline, Tetracycline |

| Lysosthapin | is a Staphylococcus simulans metalloendopeptidase. It can function as an antimicrobial against Staphylococcus aureus. |
|---|---|

Figure 14
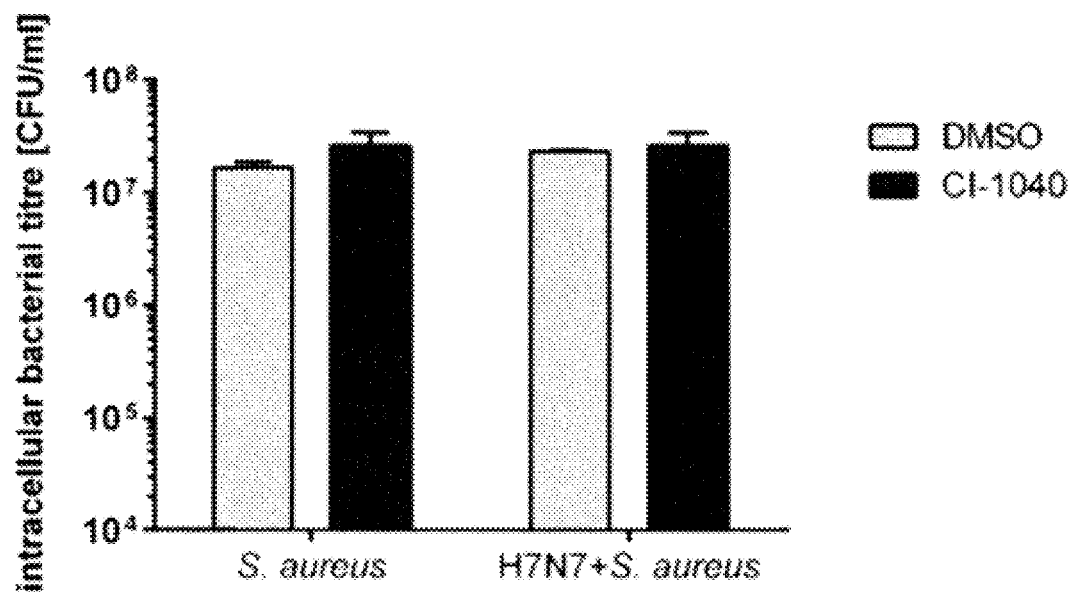
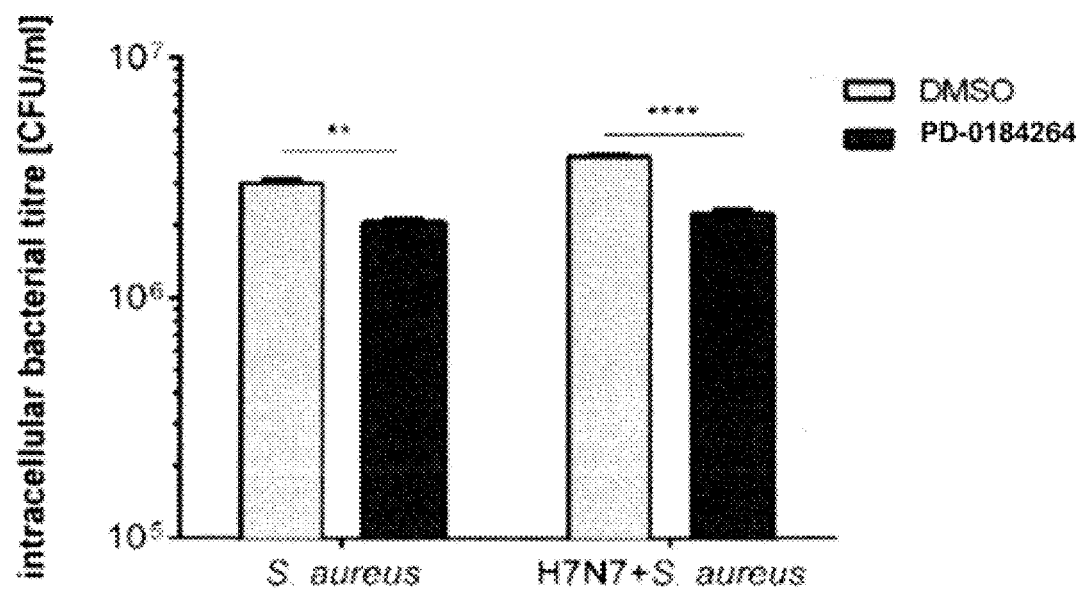

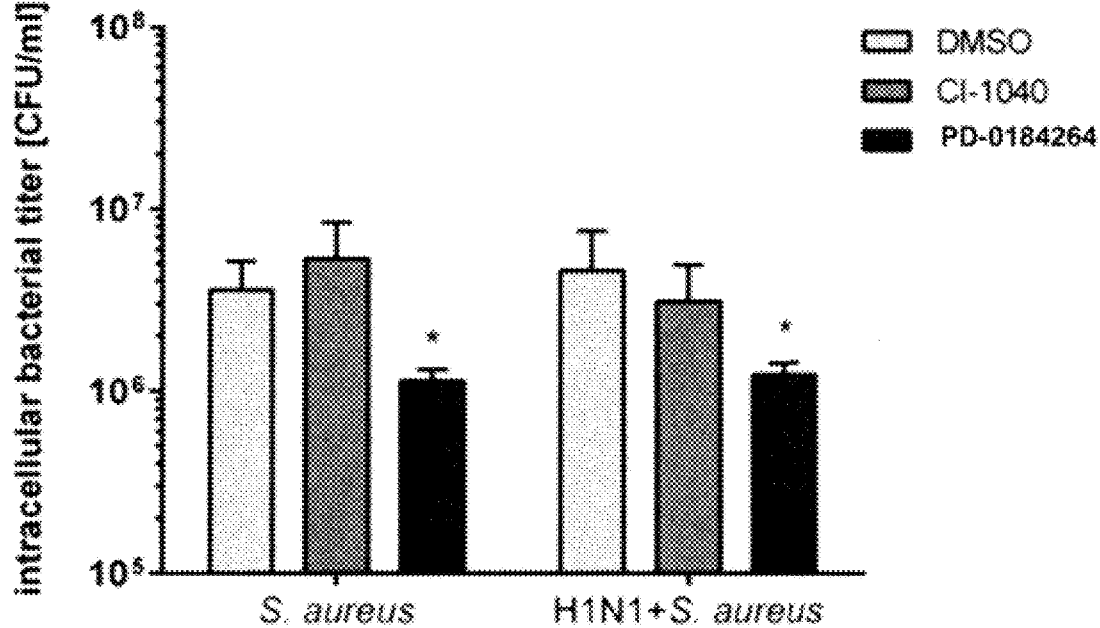

Figure 16
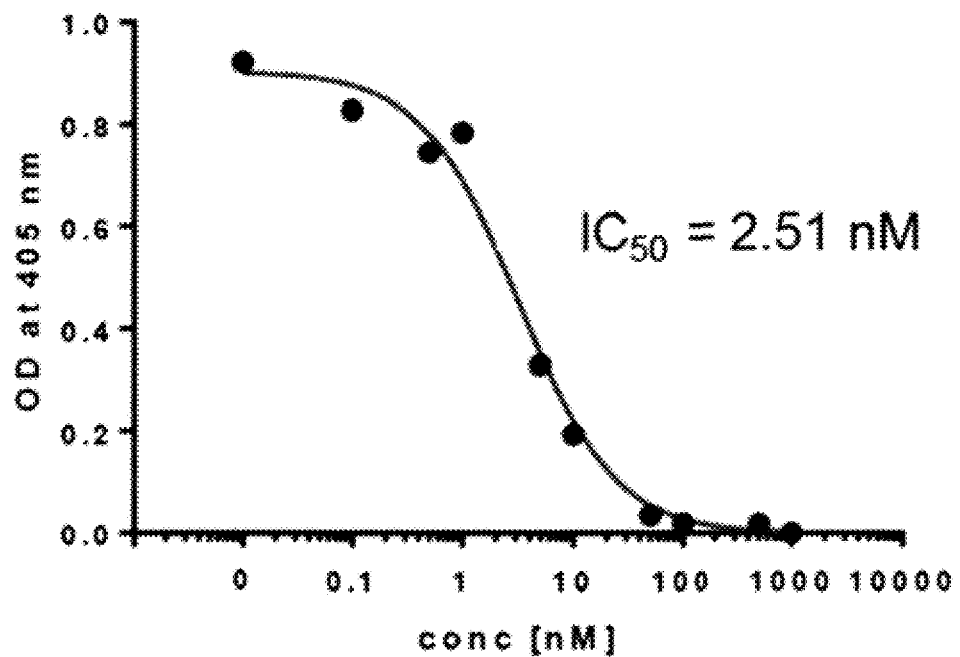
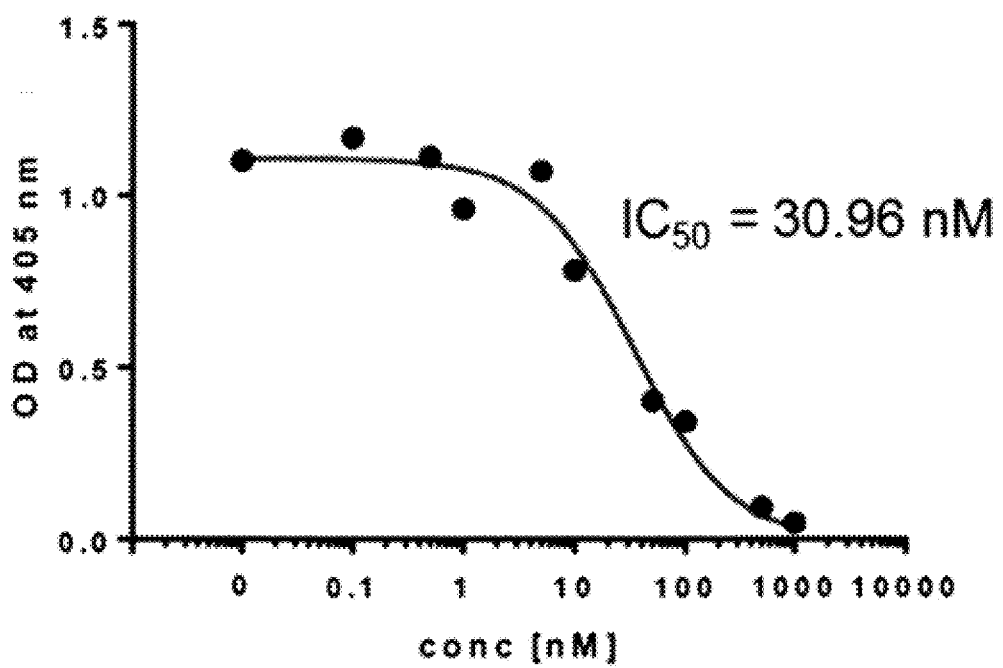

Figure 19
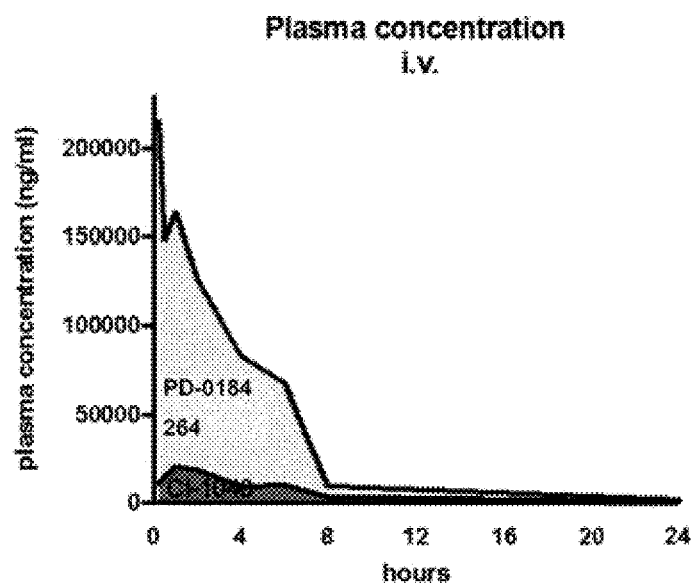
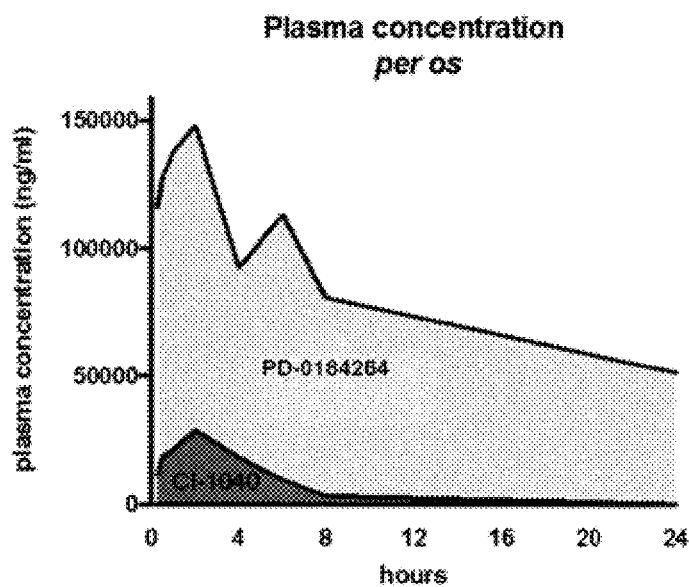

Figure 20
Start of Treatment: 24h after infection
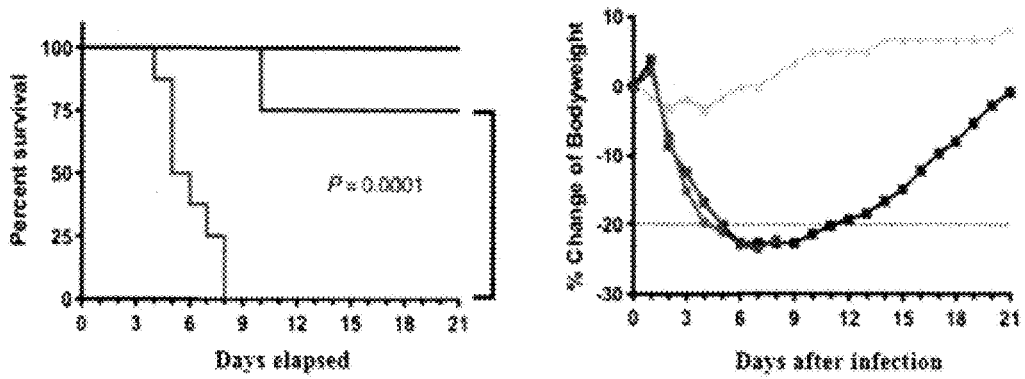
Start of Treatment: 48h after infection
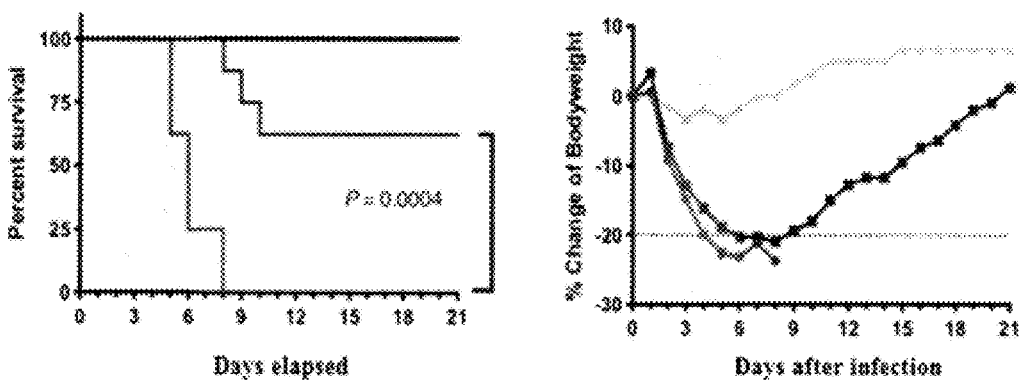
Start of Treatment: 72h after infection
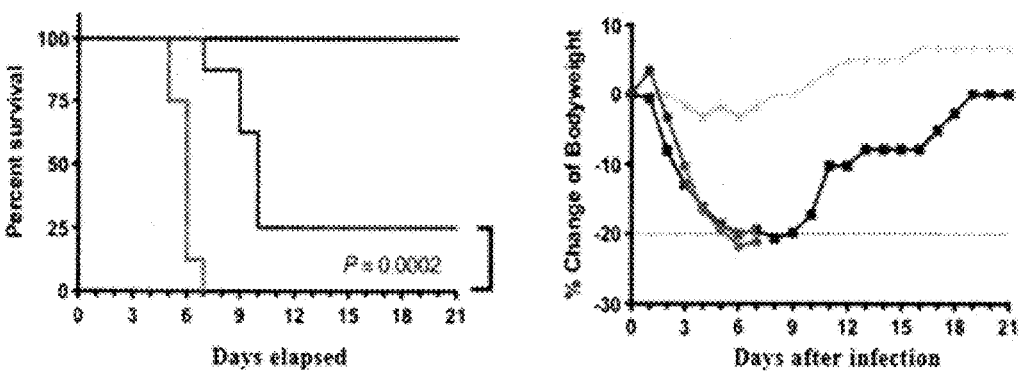
Figure legend:
— Solvent
— 25mg/Kg ATR-002
— Uninfected
Figure legend:
— Solvent
— 25mg/Kg ATR-002
— Uninfected

MEK-INHIBITOR FOR THE TREATMENT OF VIRAL AND BACTERIAL INFECTIONS

PRIORITY CLAIM

This application claims priority to International Application No. PCT/EP2020/060692, filed Apr. 16, 2020, which claims priority to Luxembourg Application No. 101183, filed Apr. 16, 2019, wherein the contents of said applications are incorporated herein by reference in their entireties.

BACKGROUND

Influenza A viruses are the causative agents of severe respiratory diseases resulting in significant morbidity and mortality. Most of the fatal cases in the course of an influenza virus infection are actually a result of secondary pneumonia caused by different bacteria, such as *Staphylococcus aureus* (*S. aureus*), *Streptococcus pneumoniae* and *Haemophilus* influenza (Morens et al., 2008, Chertow et al., 2013). The most striking problems of bacterial co-infection are the suddenly increased pathogenicity (Iwao et al., 2012, Paddock et al., 2012, Parker et al., 2012) and a limited arsenal of potent anti-infectives against the different pathogens. The high variability of influenza viruses and the continuous emergence of new strains (Neumann et al., 2009, Taubenberger et al., 2010, Parry, 2013), specific characteristics of bacterial strains (Grundmann et al. 2006, Moran et al., 2006, Gillet et al., 2007, Shilo et al., 2011), as well as the rapid resistance development of both, influenza viruses (Hayden et al, 1992, Bright et al., 2006, Pinto et al., 2006, De Clercq et al., 2007, Pinto et al., 2007) and bacteria (Grundmann et al., 2006, Moran et al., 2006, Shilo et al. 2011) against the available drugs/antibiotics are the major reasons for the poor treatment options.

WO 2001/076570 provides for the concept of treating or preventing infections caused by (−)RNA viruses, in particular by influenza viruses by way of MEK inhibitors. WO 2014/056894 provides for specific MEK inhibitors, such as AZD-6244, AZD-8330, RDEA-119, GSK-1120212 (Trametinib), GDC-0973 (Cobimetinib), CI-1040, PD-0325901, RO-5126766, MSC1936369 (AS-703026) for use in the treatment or prevention of influenza virus infections. In WO 2015/173788 A1 MEK inhibitors are disclosed for use in a method of treating influenza virus and bacterial co-infections.

The H1N1 pandemic in 2009 clearly demonstrates that Influenza A virus (IAV) has a strong impact on global health systems (Mackey and Liang, 2012; Monto et al., 2011; Robertson and Inglis, 2011). This is confirmed by the 2019/2020 coronavirus (Covid19) pandemic. Besides preventive vaccination, only a few antiviral drugs are approved for influenza and to date none are known for Covid19. This highlights the urgent need for additional effective antivirals to better control the infections. Notably, in the early phase of a pandemic, when no vaccine is available, antivirals are the stand-alone treatment. Moreover, the appearances of IAV that are resistant against currently approved antivirals underline the urgent need for new and amply available antiviral drugs (Moss et al., 2010).

However, although a few promising MEK inhibitors are already known and provided for use in treating or preventing viral infections, in particular influenza virus infections, there is still a need to provide further, ideally improved MEK inhibitors for such an application.

In addition, it is of great importance that antiviral therapy of viral infections is started as soon as possible after infection. For example, the time window to start an influenza therapy using oseltamivir is only up to 24 h. Very often, a patient visits a physician after this period of time rendering the treatment with standard anti-viral treatments futile. Further, antiviral treatments may be contraindicated because of possible drug interactions, especially in elder people, who often have to take one or more medications continuously. Very often, it is not easy to stop the taking of such medication. As a consequence, the time frame for starting an antiviral therapy already is passed before these patients are suited for antiviral therapy.

In view of the prior art, it is clear that there is the need of new compounds and compositions effective in the treatment of virus diseases in particular in respiratory tract diseases caused by RNA viruses such as influenza virus (IV) or coronaviruses (CoV), especially for late start of treatment. In addition, there is a need for treatment of virus infections, wherein the virus is resistant to antiviral therapy, and for the prevention and/or treatment of bacterial co-infections.

SUMMARY OF THE INVENTION

The solution of the technical problem is the provision of PD-0184264, a metabolite of CI-1040 for use in the treatment or prevention of viral diseases, such as influenza or coronavirus infection, bacterial infections or a co-infection comprising a bacterial infection and a viral disease. This solution is also reflected in the embodiments described hereafter and in the claims, and is illustrated in the Examples and Figures. The inventors of present application surprisingly found that the metabolite PD-0184264 of the MEK inhibitor CI-1040 has a higher antiviral and antibacterial activity than CI-1040 itself. In addition, it was shown that PD-0184264 is effective even if treatment is started more than 24 hours after infection, so that preferably, the subject has been symptomatic for a viral infection for at least 24 h, at least 36 h, at least 48 h or at least 72 h.

Preferably, the treatment is started at least 24 hours and within 48 hours post onset of disease. Preferably, the viral infection is caused by a positive or negative RNA strand virus. Preferably, the negative strand RNA virus is influenza virus, more preferably the virus is influenza A virus (IAV) or influenza B virus (IBV), even more preferably, the influenza A virus is selected from the group consisting according to H1N1, H2N2, H3N2, H5N6, H5N8, H6N1, H7N2, H7N7, H7N9, H9N2, H10N7, N10N8 or H5N1 or the Influenza B virus is selected from the group consisting of IBV type Yamagata and Victoria. Preferably, the positive strand RNA virus is a coronavirus such as severe acute respiratory virus (SARS-CoV and SARS-CoV2) or Middle East respiratory syndrome coronavirus (MERS).

In some embodiments, the virus is resistant to antiviral treatment, wherein more preferably the antiviral treatment is administration of oseltamivir, zanamivir, peramivir, amantadine, rimantadine, favipiravir, baloxavir marboxil or pimodivir.

In one embodiment, the virus resistant to antiviral treatment is a H1N1 H275Y mutant.

Therefore, the use of PD-0184264 solves the technical problem underlying the present application by providing a more effective treatment option for viral infections, in particular influenza virus infections, as well as for viral, in particular influenza virus, bacterial co-infections, with an enlarged treatment window allowing for start of treatment more than 24 hours and up to at least 72 hours after the first symptoms were identified.

Although, the MEK inhibitor CI-1040 is already effective in the treatment or prevention of influenza virus infection and influenza virus or bacterial co-infection, the inventors found that a metabolite (PD-0184264, formula 1) of CI-1040 is more effective in targeting influenza virus or co-infections comprising an influenza virus and a bacterial infection than CI-1040 itself. PD-0184264 is one of several metabolites of CI-1040 (Wabnitz et al., 2004, LoRusso et al., 2005), but it could neither be known nor assumed that a metabolite is more potent than CI-1040. Much to the surprise of the inventors, they indeed found that one metabolite (PD-0184264, structure 1 below) is more effective and has a higher therapeutic potential than CI-1040 as shown in the examples. This property of PD-0184264 could not be expected, since PD-0184264 actually shows a weaker inhibitory effect on MEK kinases in vitro than CI-1040 (see Example 9). In addition, in vitro assays showed a weaker antiviral effect of PD-0184264 in comparison to CI-1040 (see Example 10) while in vivo assays surprisingly showed a much stronger antiviral effect of PD-0184264 in comparison to CI-1040 (see Example 11).

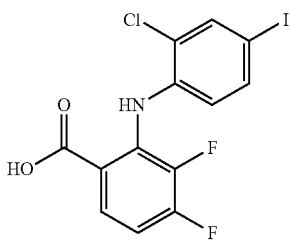

1

Accordingly, the present invention relates to PD-0184264 or a pharmaceutically acceptable salt thereof for use in a method for the prophylaxis and/or treatment of a bacterial infection and/or a viral disease. Preferably, the virus causing the viral disease is an RNA virus. When the RNA virus is a negative strand RNA virus, it is preferably influenza virus and more preferably influenza A or influenza B virus. When the RNA virus is a positive strand RNA virus, the virus is preferably a coronavirus such as SARS, SARS-CoV2 or MERS.

The present invention also relates to PD-0184264 or a pharmaceutically acceptable salt thereof for use in a method for the prophylaxis and/or treatment of a bacterial infection. The bacterial infection is preferably mediated by a bacterium selected from the group consisting of Staphylococcaceae, Streptococcaceae, Legionellaceae, Pseudomonadaceae, Bacillaceae, Chlamydiaceae, Mycoplasmataceae, Enterobacteriaceae, Pseudomonadales and/or Pasteurellaceae.

The present invention further relates to PD-0184264 or a pharmaceutically acceptable salt thereof for use in a method for the prophylaxis and/or treatment of a co-infection comprising a bacterial infection and a viral disease.

Preferably, PD-0184264 or pharmaceutically acceptable salt thereof is for use in a method for the prophylaxis and/or treatment of a co-infection comprising a bacterial infection and a viral disease, wherein the bacterial infection is mediated by a bacterium selected from the group consisting of Staphylococcaceae, Streptococcaceae, Legionellaceae, Pseudomonadaceae, Bacillaceae, Chlamydiaceae, Mycoplasmataceae, Enterobacteriaceae, Pseudomonadales and/or Pasteurellaceae.

Preferably, PD-0184264 or a pharmaceutically acceptable salt thereof is for the use in a method for the prophylaxis and/or treatment of a co-infection comprising a bacterial infection and a viral disease, wherein the virus is a negative strand RNA virus, preferably an influenza virus, more preferably influenza A virus or influenza B virus.

Preferably, PD-0184264 or a pharmaceutically acceptable salt thereof is for use in a method for the prophylaxis and/or treatment of a viral disease, wherein PD-0184264 or a pharmaceutically acceptable salt thereof is administered in combination with a neuraminidase inhibitor or a pharmaceutically acceptable salt thereof.

Preferably, PD-0184264 or a pharmaceutically acceptable salt thereof is for use in a method for the prophylaxis and/or treatment of a co-infection comprising a bacterial infection and a viral disease, wherein PD-0184264 or a pharmaceutically acceptable salt thereof is administered in combination with a neuraminidase inhibitor or a pharmaceutically acceptable salt thereof.

In an alternate embodiment PD-0184264 or a pharmaceutically acceptable salt thereof is for the use in a method for the prophylaxis and/or treatment of a viral disease or in a method for the prophylaxis and/or treatment of a co-infection comprising a bacterial infection and a viral disease, wherein the neuraminidase inhibitor is selected from oseltamivir, oseltamivir phosphate, zanamivir, laninamivir or peramivir or a pharmaceutically acceptable salt thereof.

Also provided for by the present invention is a pharmaceutical composition comprising PD-0184264 or a pharmaceutically acceptable salt thereof and a neuraminidase inhibitor or a pharmaceutically acceptable salt thereof.

Preferably, PD-0184264 is for use in a method for the prophylaxis and/or treatment of a viral disease and/or in a method for the prophylaxis and/or treatment of a bacterial diseases and/or in a method for the prophylaxis and/or treatment of a co-infection comprising a bacterial infection and a viral disease, wherein PD-0184264 is combined with one or more MEK inhibitors.

Preferably, PD-0184264 or a pharmaceutically acceptable salt thereof is for the use in prophylaxis and/or treatment of a bacterial infection, a viral infection or a co-infection in a subject, preferably a vertebrate, more preferably a bird or a mammal, most preferably a human.

The present disclosure further relates to a method of treating a bacterial infection in a subject comprising administering a therapeutically effective amount of PD-0184264 or a pharmaceutically acceptable salt thereof to the subject in need thereof.

Additionally, the present invention relates to a method of treating a viral disease in a subject comprising administering a therapeutically effective amount of PD-0184264 or a pharmaceutically acceptable salt thereof to the subject in need thereof. In a preferred embodiment, PD-0184264 is administered to the subject once daily in an oral dosage form of 100 mg to 900 mg, preferably 600 mg.

In a further embodiment, the present invention relates to a method of treating a co-infection comprising a bacterial infection and a viral disease in a subject, the method comprising administering a therapeutically effective amount of PD-0184264 or a pharmaceutically acceptable salt thereof to the subject in need thereof.

Preferably, the virus is a negative strand RNA virus, more preferably the virus is influenza virus and most preferably, the influenza virus is influenza A virus or influenza B virus.

Preferably, the bacterial infection is mediated by a bacterium selected from the group consisting of Staphylococcaceae, Streptococcaceae, Legionellaceae, Pseudomonadaceae, Bacillaceae, Chlamydiaceae, Mycoplasmataceae, Enterobacteriaceae, Pseudomonadales and Pasteurellaceae.

BRIEF DESCRIPTION OF THE DRAWINGS

The figures show:

FIG. 6: Comparison of the antibacterial action of PD-0184264 to the common antibiotics.
To align the antibacterial properties of the MEK-inhibitor PD0184164 with the action of a common antibiotic, we treated bacteria over-night with solvent, the MEK-inhibitors U0126 and PD-0184264 or different concentrations of the antibiotic gentamicin. In comparison with the solvent treated bacteria, incubation with the first generation MEK-inhibitor U0126 resulted only in a minor reduction in bacterial titers, whereas treatment with PD-0184264 led to a very strong reduction in bacterial load. This was true for both bacterial strains.

FIG. 12: Table 1: antibiotics.

FIG. 14: Graph showing the changes in intracellular bacterial load upon treatment with CI-1040 (a) or PD-0184264 (b).
Comparable results were obtained when CI-1040 or PD-0184264 were administered at later times during on-going infection (c).

FIG. 16: Cell free kinase assay showing the inhibitory effects of CI-1040 and PD-0184264 on the MEK pathway.
The activity of the kinases is measured by determining the amount of phosphorylated target protein ERK by an ELISA assay. Three independent experimental series were performed showing similar results. One representative experiment is presented here.

FIG. 19: PD-0184264 has a better bioavailability than CI-1040.
(A) Male NMRI mice were treated with either 75 mg/kg CI-1040 (dark grey area) or with 75 mg/Kg PD-0184264 the intravenous route. Blood was collected at 15 min, 30 min, 1 h, 2 h, 4 h, 6 h, 8 h and 24 h (test day 2) after administration and plasma was analysed for the presence of the drug. (B) Male NMRI mice were treated with either 150 mg/kg CI-1040 (dark grey area) or with 150 mg/kg PD-0184264 per os using oral gavage. Blood was collected at 15 min, 30 min, 1 h, 2 h, 4 h, 6 h, 8 h and 24 h (test day 2) after administration and plasma was analysed for the presence of the drug.

FIG. 20: Survival of mice after treatment with PD-0184264.
Eight female C57BL/6 mice were infected with H1N1pdm09 infection
and treated with 25 mg/kg PD-0184264 (ATR-002, Middle grey line) or with solvent alone (light grey line) via the oral route. Treatment started 24, 48 or 72 hours after infection for five days as indicated in the graphs (grey bar). Mice had to be sacrificed, when a bodyweight reduction of 20% was found (grey dotted line). Graphpad Prism 8 software was used to illustrate both figures. P-value was determined using Logrank (Mantel-Cox) test.

DETAILED DESCRIPTION

The following description includes information that may be useful in understanding the present invention. It is not an admission that any of the information provided herein is prior art or relevant to the presently claimed inventions, or that any publication specifically or implicitly referenced is prior art.

The above being said, the present invention relates to PD-0184264 for use in a method of treatment of a viral disease or a co-infection comprising a bacterial infection and a viral infection. As shown in the examples, PD-0184264 appears to act on bacterial kinase PknB and thereby at least in part may exert its bacteriostatic effect.

Also, as demonstrated in the appended Examples, PD-0184264 shows an effect in viral and bacterial infection scenarios as well as in bacterial and viral co-infection scenarios. This effect is surprisingly stronger than of CI-1040, a MEK inhibitor already known in the prior art for the treatment of bacterial and viral infections. When comparing the inhibitory effect of CI-1040 and PD-0184264 on a MEK kinase as shown in Example 9, one would actually expect the opposite, since MEK inhibitors were used in prior art to achieve said effects.

Figure 1:
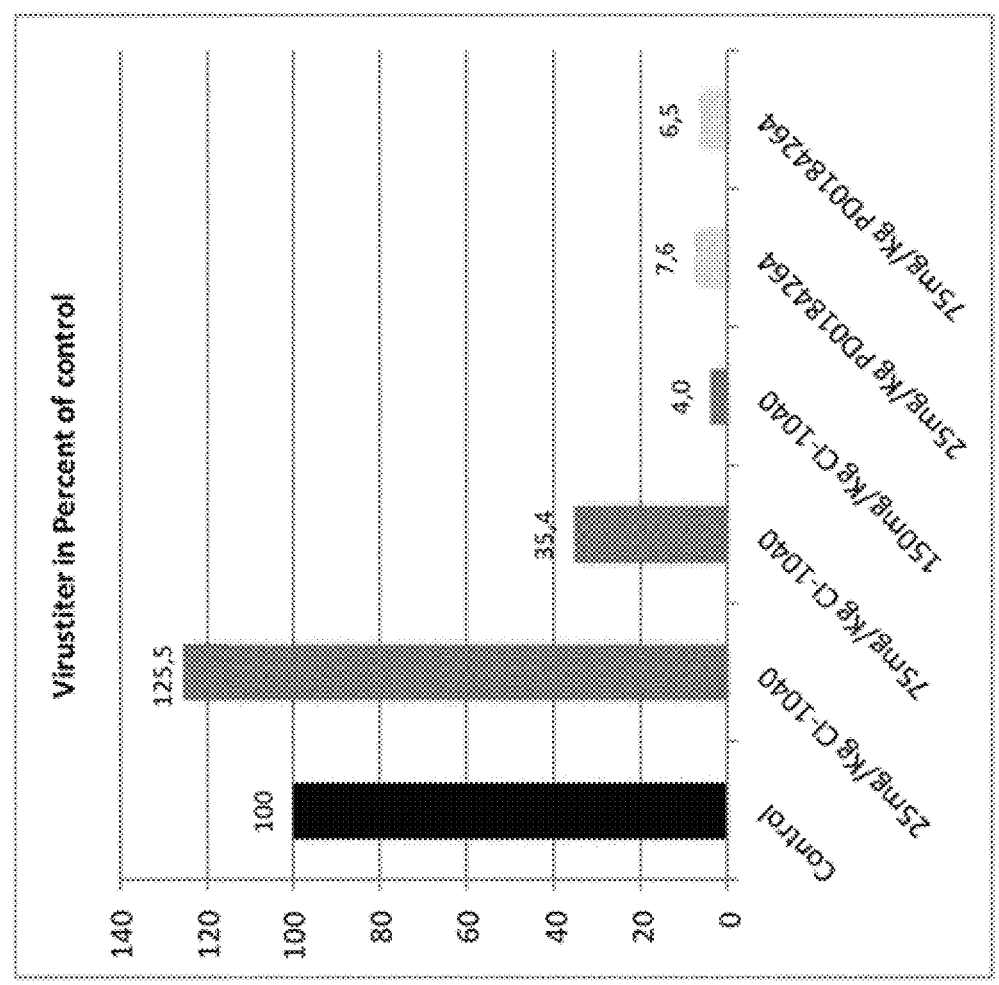
FIG. 1: Treatment of mice infected with Influenza A with PD-0184264 or CI-1040.
Results from the experiment of Example 1 are presented as virus titer (log 10) pfu/ml (left) or % virus titer (right).
Figure 18:
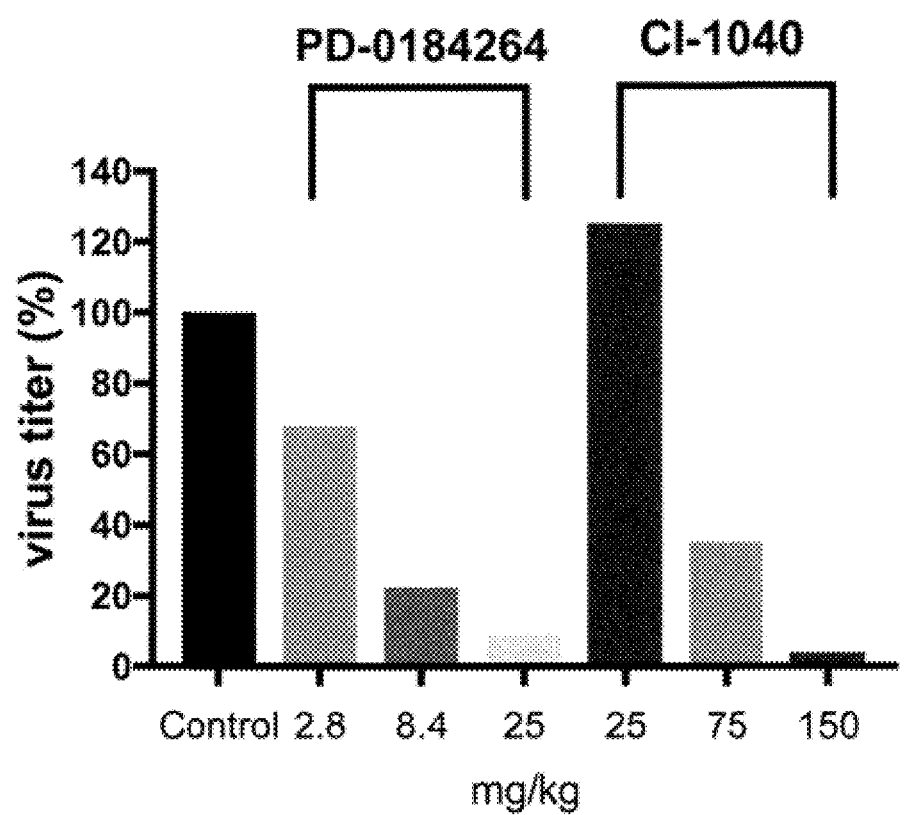
FIG. 18: In vivo reduction of virus titer in the lung of mice by PD-0184264.
After H1N1pdm09 virus infection female C57BL/6 mice were treated with 2.8, 8.4 or 25 mg/kg PD-0184264 (left panel) or with 25, 75 or 150 mg/Kg CI-1400 (right panel) the oral route. 24 h after infection the animals were killed and virus titer was determined using the standard method.

The same is true when comparing the antiviral effect of PD-0184264 and CI-1040 in in vitro assays. Here, CI-1040 is more effective than PD-0184264 as can be seen from Example 10. Specifically, a 10-fold higher concentration of PD-0184264 is needed in an in vitro assay to achieve the same inhibitory effect. Surprisingly, it was found that despite the weak in vitro inhibition, PD-0184264 is superior to CI-1040 in vivo as can be seen from Example 11. As shown in FIG. 18, already 2.8 mg/kg PD-0184264 show a reduction of the virus titer, whereas 25 mg/kg PD-0184264 show a at least 90% reduction of the virus titer in the lung. In contrast, CI-1040 shows a similar reduction only at 150 µM. Furthermore, Example 1 shows a reduction of virus titer in the lung by PD-0184264. In Example 1, mice were infected with an influenza virus and treated with 150 mg/kg, 75 mg/kg, or 25 mg/kg CI-1040 or PD-0184264 respectively. As shown in FIG. 1, already 25 mg/kg PD-0184264 have the same effect as 150 mg/kg CI-1040. Thus, much to the surprise of the inventors, PD-0184264 shows a strong antiviral effect in vivo although previous in vitro data did not provide any incentive to continue the work with PD-0184264. This surprising effect may be based on a higher bioavailability of PD-0184264 in comparison to CI-1040, which is shown in Example 12.

Figure 2:
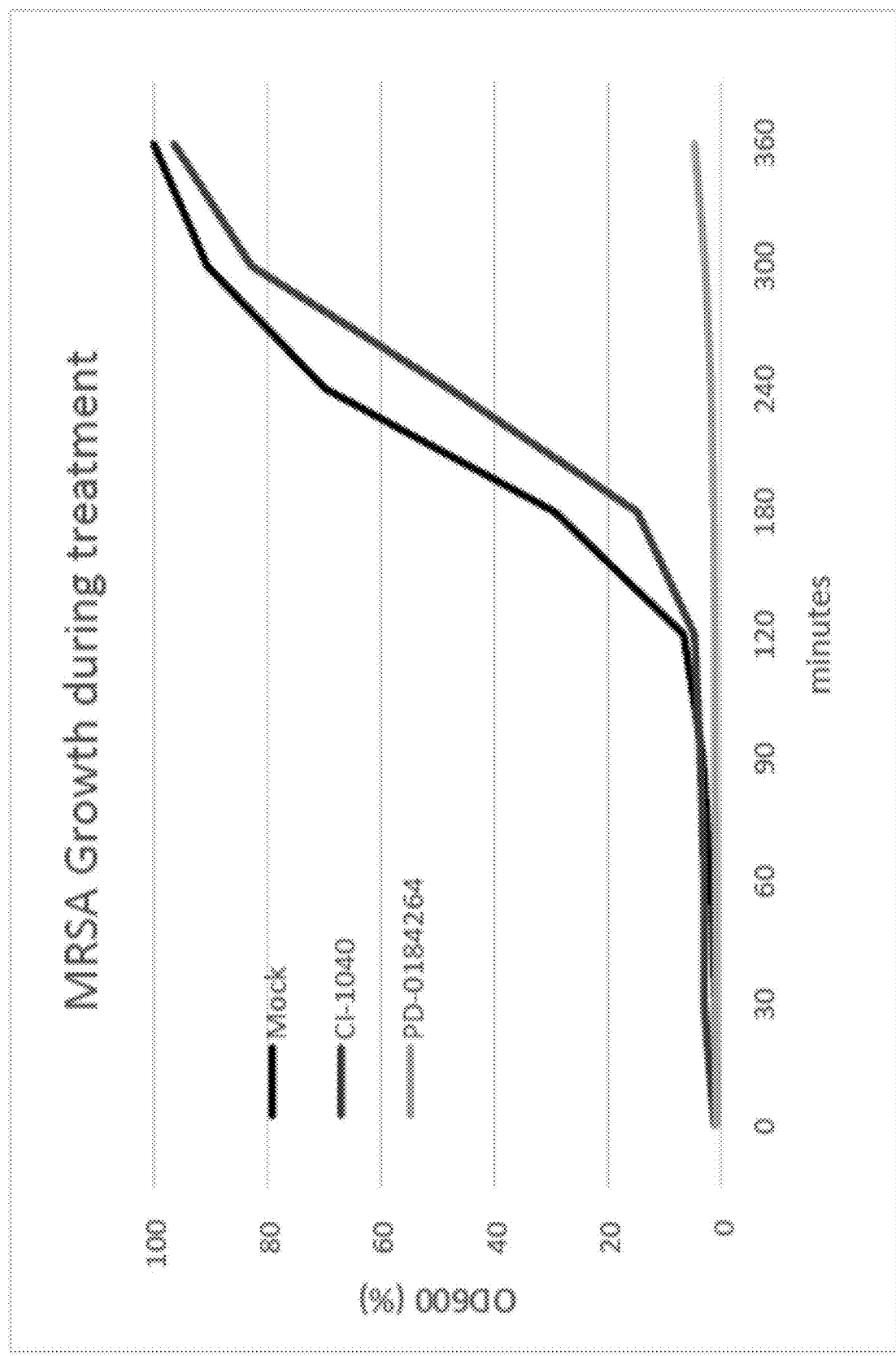
FIG. 2: Graph showing the impact of PD-0184264 and CI-1040 on MRSA bacterial growth.
At different time points, as indicated in the horizontal axis of the graph, the optical densities of the cell free bacterial cultures were measured as an indication for bacterial growth, shown on the vertical axis of the graph in % (OD600). Data represent the mean value of three biological replicates described in Example 2.
Figure 3:
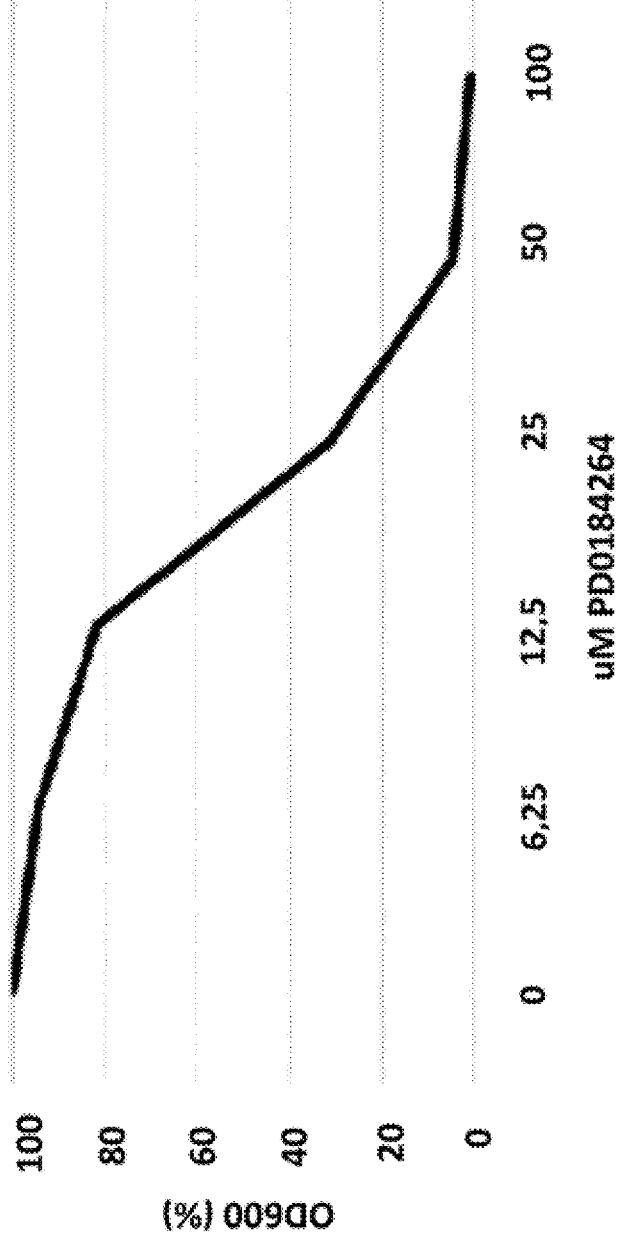
FIG. 3: Inhibition of bacterial MRSA growth with different concentrations of PD-0184264.
PD-0184264 was administrated in different concentrations (as indicated) to an over-night culture of S. aureus USA300 (MRSA). After 6 hrs the optical density was tested. Data shown in the figure represents one experiment out of three biological replicates described in Example 2.
Figure 4:
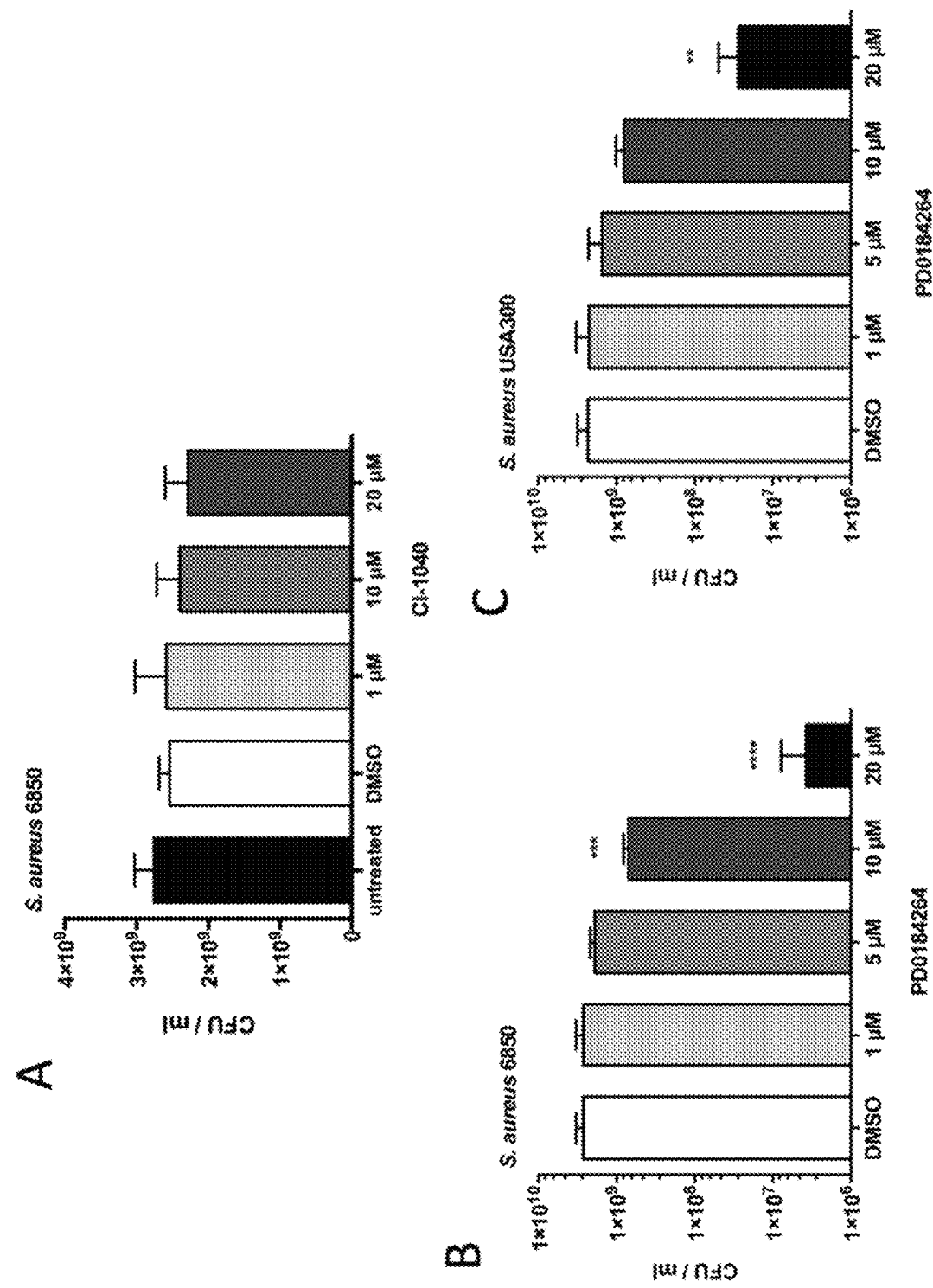
FIG. 4: The impact of CI-1040 and PD-0184264 on bacterial growth.
(A) Impact of CI-1040 on bacterial growth at different concentrations (B, C) Impact of PD-0184264 on S. aureus strain 6850 (B) or strain USA300 (C) at different concentrations of PD-184264.
Figure 7:
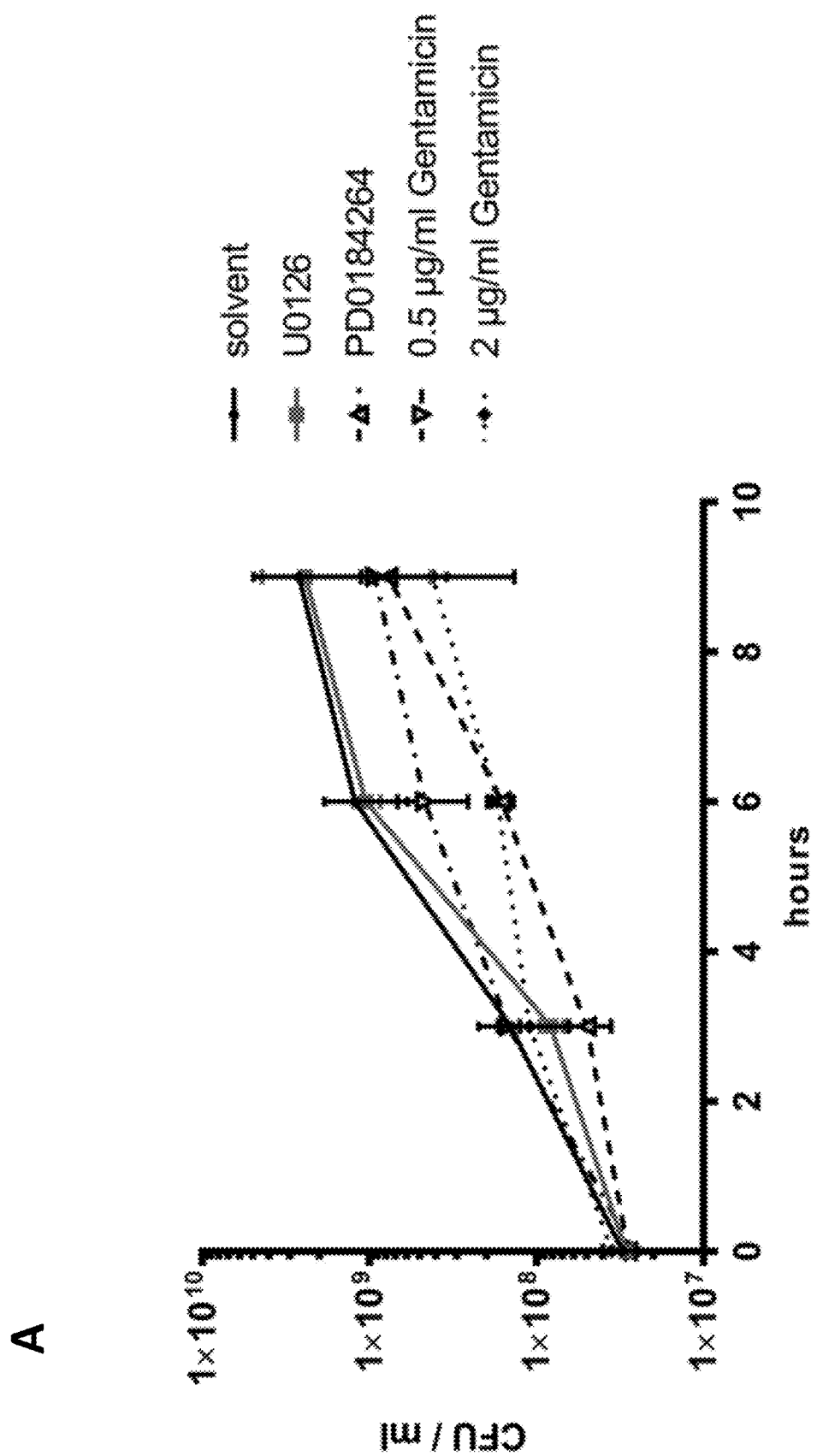
FIG. 7: (a) Results of time-of-addition assays comparing the antibacterial action of the PD-0184264 with other MEK-inhibiting compounds or the antibiotic gentamycin.
(b) Results of a test for resistance to the MEK inhibitor PD0184264 in S. aureus compared to treatment with Gentamicin, Erythromycin or untreated.
Figure 7:
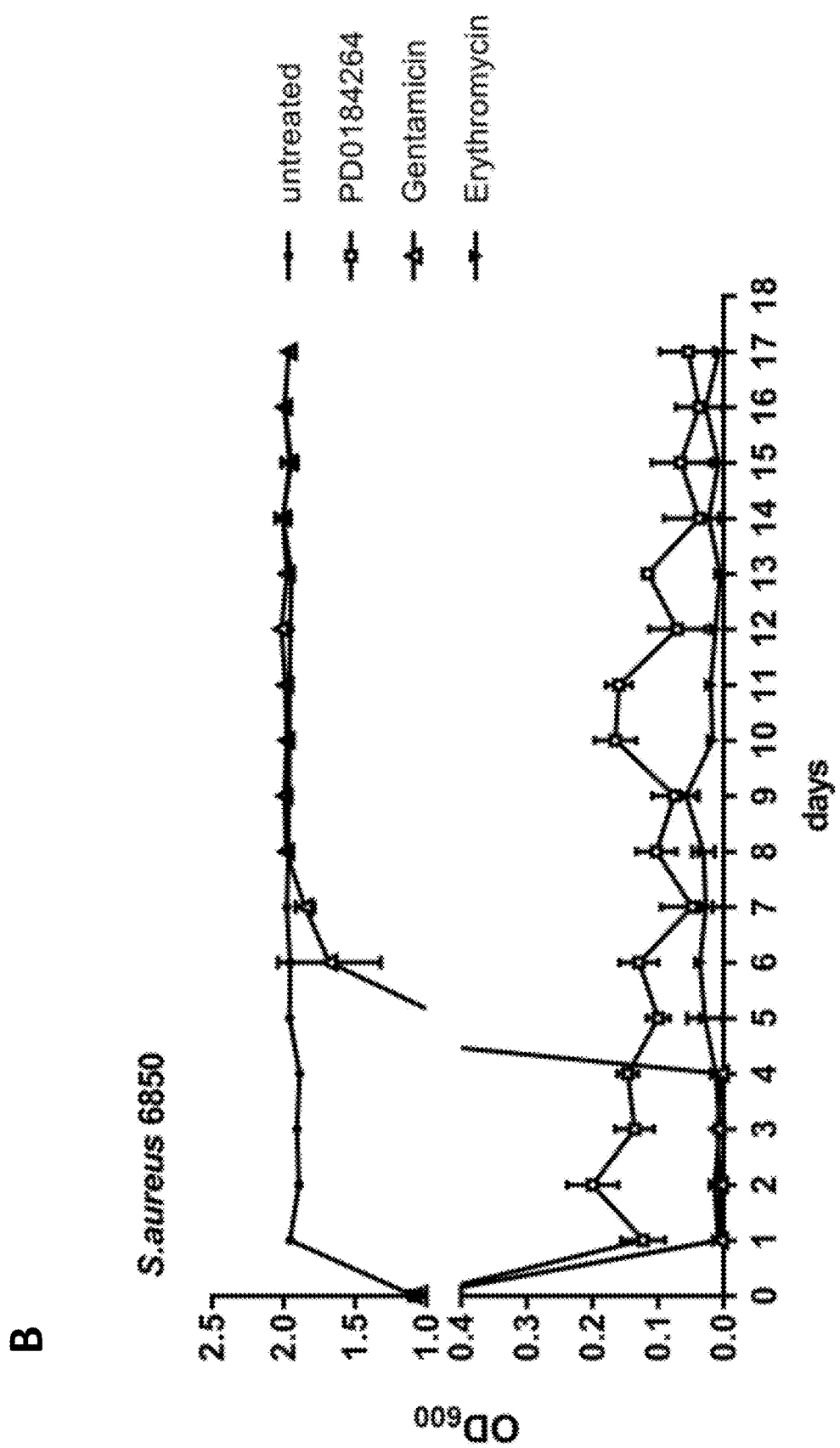
Figure 9:
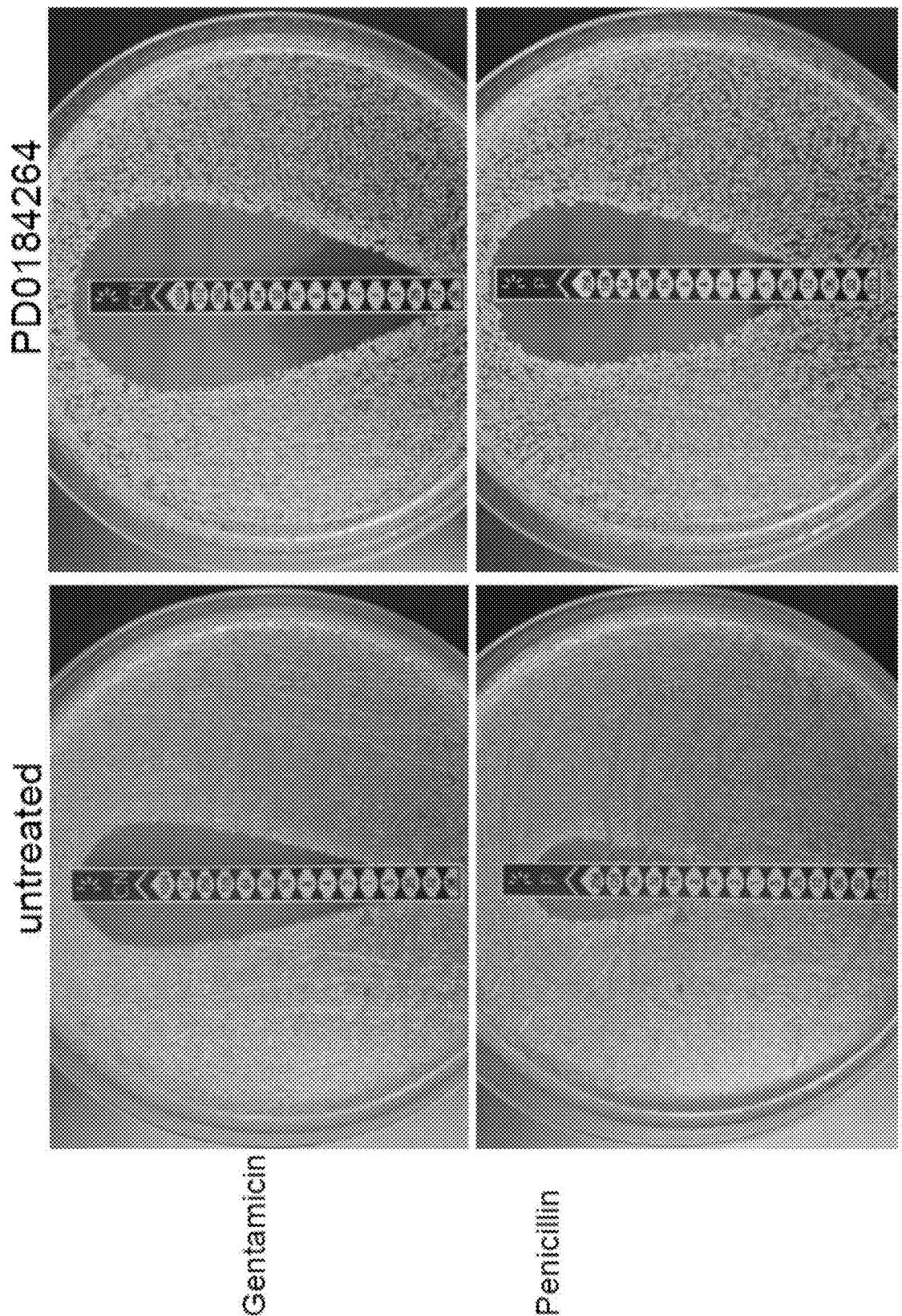
FIG. 9: Determination of the impact of inhibitor treatment on the minimal inhibitory concentration (MIC) of different antibiotics.
Figure 10:
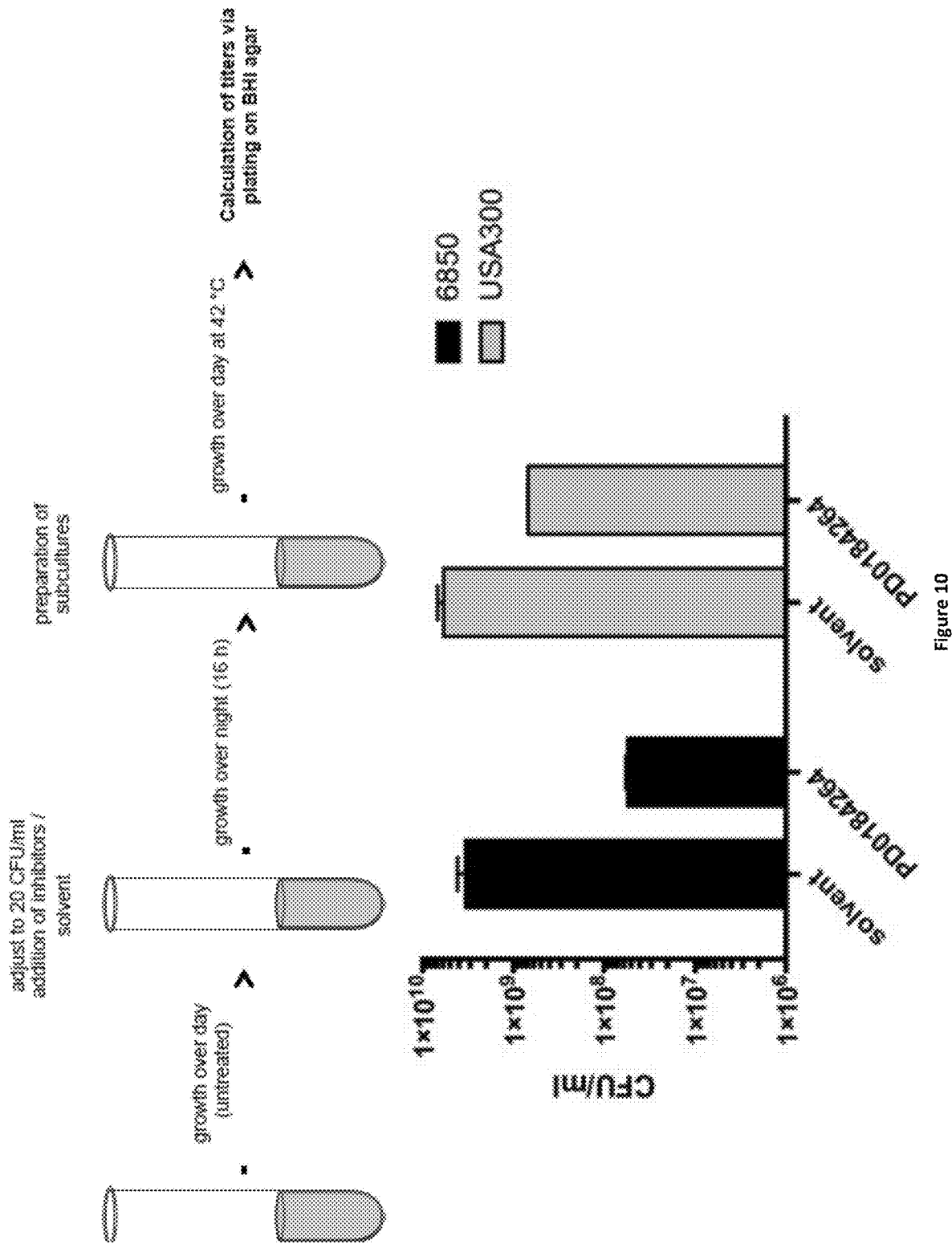
FIG. 10: Stress tolerance of S. aureus strain 6850 and MRSA strain USA300 when treated with PD-0184264.

Examples 2, 4, and 6-8 additionally show the strong antibacterial effect of PD-0184264, also in comparison to CI-1040 and other MEK inhibitors. In Example 2, the effect of PD-0184264 on bacterial growth is analyzed. FIG. 2 shows that PD-0184264 inhibits the growth of bacteria whereas CI-1040 has no effect on bacterial growth. In FIG. 3 it is shown that bacterial growth is inhibited by PD-0184264 in a concentration-dependent manner showing an almost complete inhibition of growth starting at 50 µM PD-0184264. Similarly, also FIG. 4 shows that bacterial growth is inhibited by PD-0184264 in a concentration-dependent manner—already 10 µM PD-0184264 show a significant reduction of growth—whereas CI-1040 has no effect on bacterial growth. In Example 4, the antibacterial effect of PD-0184264 is compared to MEK inhibitor U0126 or the antibiotic gentamycin. FIG. 6 shows that PD-184264 has a similar antibiotic effect as gentamycin whereas the MEK inhibitor U0126, known from prior art, has no effect on bacterial growth. The same is true for FIG. 7A, in which the course of bacterial growth is monitored. In FIG. 7B it is additionally shown that PD-0184264 does not induce resistance against PD-0184264 whereas the bacteria readily develop resistances against gentamycin and erythromycin. Thus, PD-0184264 does not induce resistance in bacteria. In Example 6 the influence of PD-0184264 on the sensitivity of bacteria to an antibiotic was analyzed. As shown in FIG. 9 and Table 2, treatment with PD-0184264 indeed led to an increase in susceptibility of the bacteria to different antibiotics, which was most prominent in case of penicillin and gentamicin. Additionally, FIG. 10 shows that PD-0184264 decreases the stress tolerance of bacteria. Example 7 provides evidence that the effect of PD-0184264 is not restricted to *S. aureus* but also has an effect in other bacteria such as *Streptococcus pneumoniae* (see FIGS. 11A and B) and *Bacillus subtilis* (see FIG. 11C).

Figure 5:
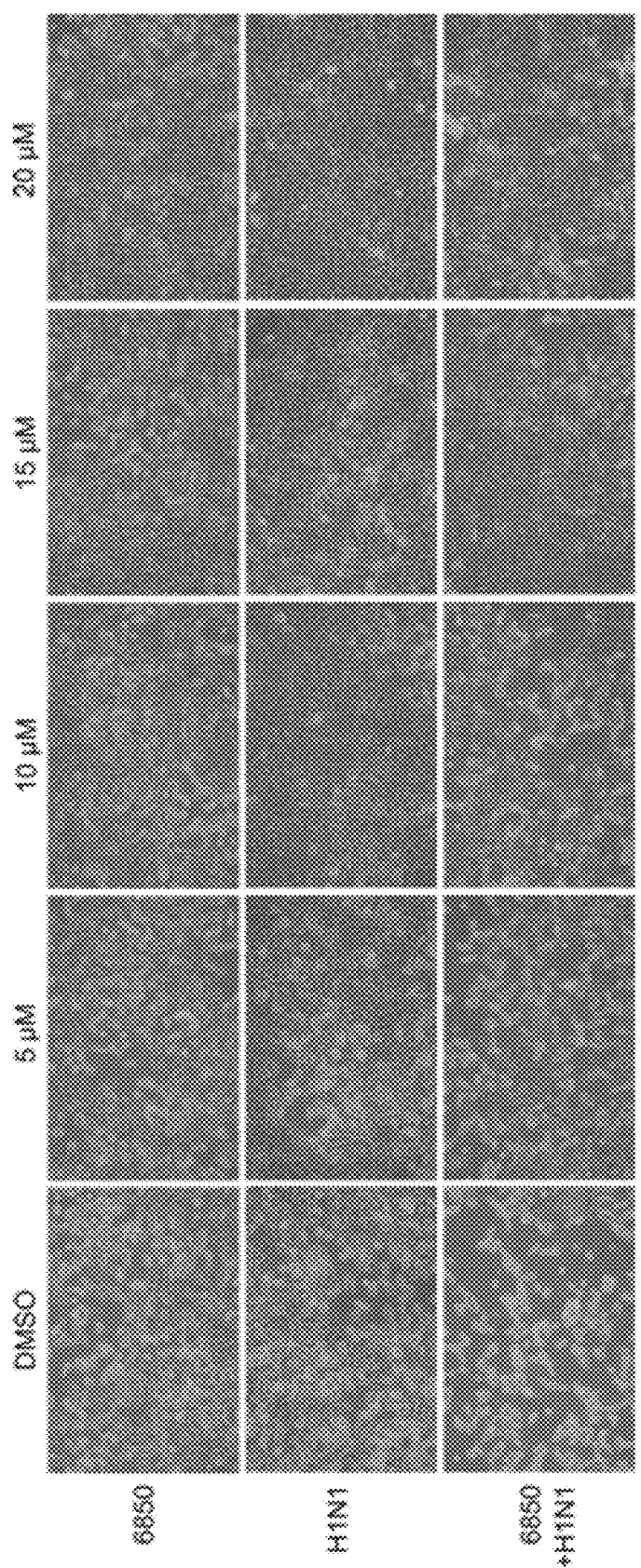
FIG. 5: Administration of PD-0184264 to singular or co-infected cells protects cells.
Human lung epithelial cells (A549) were pretreated with PD-0184264 (at the concentrations indicated) or solvent (DMSO) and infected with human influenza virus strain A/Puerto Rico/8/34 (H1N1). Given the antiviral and the strong antibacterial effect of PD-0184264 (FIG. 2 to 4) we analyzed whether this feature of the compound could also be observed macroscopically with regard to the cell disrupting cytopathic effects (CPE) elicited by IAV (influenza A virus) and/or S. aureus infection. A slight disruption of the cell monolayer was observed following singular infection with IAV (H1N1) (middle panel) or the S. aureus strain 6850 (upper panel). This CPE was strongly increased upon co-infection with both pathogens (lower panel), but was inhibited in the presence of increasing concentrations of PD-0184264.
Figure 15:
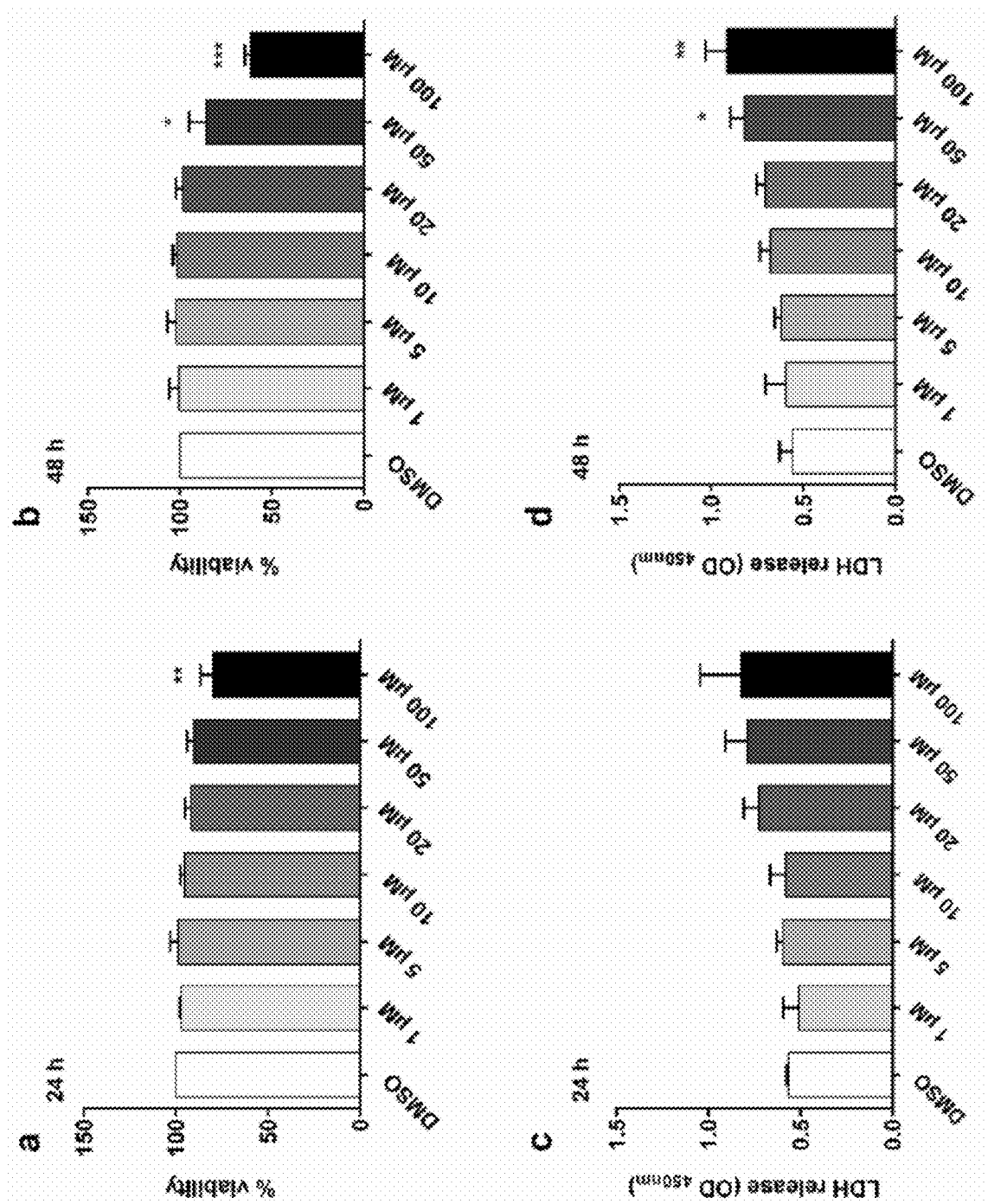
FIG. 15: Graph showing cell viability (A, B) and membrane rupture (C, D).
(A, B) show the A549 Cell viability in presence of increasing concentrations of PD-0184264. In (C) and (D), an LDH-Assay was performed to determine membrane rupture due to inhibitor treatment.

Examples 3 and 8 underline the efficacy of PD-0184264 within the context of a bacterial and viral co-infection. Example 3 analyzed whether the efficacy of PD-0184264 could also be observed macroscopically with regard to the cell disrupting cytopathic effects (CPE) elicited by viral and/or bacterial infection. FIG. 5 shows that PD-0184264 reduces the cytopathic effect elicited especially by a bacterial and viral co-infection in a concentration-dependent manner showing effects already at 15 µM PD-0184264. The same was also analyzed in Example 8, which shows in FIG. 13 again the positive effect of PD-0184264 in a bacterial and viral co-infection scenario. Example 8 further analyzed the effect of PD-0184264 on intracellular bacterial titer in a co-infection scenario. FIG. 14 shows that PD-0184264 reduces the intracellular bacterial titer while CI-1040 has no effect. Additionally, Example 8 and FIG. 15 show that PD-0184264 exerts no cytotoxic effect.

Further, in Example 13, it was shown that PD-0184264 treatment of mice infected with an H1N1 influenza strain leads to a significant difference in survival, even though the drug was administered as late as 72 hours after infection (see FIG. 20).

The results are comparable to data obtained with CI-1040 presented in the Haasbach paper (Haasbach et al. 2017) and in further experiments performed by the applicant. In these experiments, it was found that CI-1040 has an enlarged treatment window over known anti-virals, and specifically Tamiflu (oseltamivir), allowing for administration at a time period when Tamiflu is ineffective. Using a mouse model, the inventors demonstrated that CI-1040 can reduce influenza virus lung titers in vivo. Surprisingly, the treatment window for CI-1040 was found to expand to at least 48 h post infection when Tamiflu® treatment has no effect.

According to the FDA label, oseltamivir (Tamiflu®) is currently indicated for the treatment of influenza in patients who have been symptomatic for no more than 2 days. This corresponds to what was observed in the mouse model in previous studies, where oseltamivir is no longer effective if it is administered more than 48 h post infection with influenza virus. In contrast, PD-0184264 was effective even 72 h post infection. Hence, it has been shown that PD-0184264, like CI-1040, has a longer treatment window than oseltamivir. For this reason, it is likely that the effects observed in the mouse model can be extrapolated to human patients, meaning that PD-0184264 or a pharmaceutically acceptable salt or a derivative thereof can be administered to patients more than 2 days after onset of symptoms of a viral infection. This also makes sense when the method of action of CI-1040 and PD-0184264 is compared to that of oseltamivir. As mentioned above, oseltamivir is thought to block the elution of virions from the infected cells. For this reason, it is only effective if the virions have not yet left the cell. It was found that CI-1040 and PD-0184264, by contrast, blocks the MEK pathway that is necessary for viral replication, so that the viral RNP complexes are retained in the cell nucleus. Regarding the molecular mode of action of MEK inhibition, the inventors have previously shown that inhibition of the kinase with the prototype inhibitor U0126 leads to a blockade of nuclear cytoplasmic transport of viral RNP complexes (Pleschka et al., 2001). This could be confirmed for CI-1040 and PD-0184264. It is expected, based on the data in Example 13 and further preliminary studies that PD-0184264 will have the same effect as CI-1040, as it is a metabolite of CI-1040 and targets the same pathway as CI-1040.

Thus the methods and uses of the invention also relate to treating a viral infection in subjects that have been symptomatic for at least 24 hours, at least 36 hours, or at least 48 hours. These times of course include all time frames in between, such as 25, 26, 27, 28, 29, 30, 31, 32, 33, 34, 35, 37, 38, 39, 40, 41, 42, 43, 44, 45, 46 or 47 hours for the subject being symptomatic. In a preferred embodiment, the subject has been symptomatic for at least 48 hours before treatment. For example, treatment can be started between 24 and 48 hours after onset of disease. In this context it should be noted that "being symptomatic" and "onset of disease" can be used interchangeably. However, the treatment could also be started at least 60 h, at least 72 h or at least 96 h post infection. In cases where PD-0184264 or a pharmaceutically acceptable salt or derivative thereof is administered when a different antiviral was already found to be ineffective, PD-0184264 or a pharmaceutically acceptable salt or derivative thereof can be administered after 24 hours, when the treatment with the previous antiviral has been completed.

In addition it is quite likely that like CI-1040, PD-0184264 is also effective against influenza viruses, which are resistant to antiviral treatment. This is a feature of CI-1040 and PD-0184264 that solves a problem of many standard antiviral treatments and allows CI-1040 and PD-0184264 to be administered after treatment with standard antivirals has failed. Standard antiviral treatment as used herein is defined as a treatment with a drug that has been approved for use as an antiviral and which is effective in inhibiting the development of the viral pathogen at any step of its life cycle. Examples include entry inhibitors, uncoating inhibitors, inhibitors of reverse transcription, polymerase inhibitors, endonuclease inhibitors, protein maturation inhibitors, integrase inhibitors, transcription inhibitors, translation inhibitors, protease inhibitors, virion assembly inhibitors or virion release inhibitors. In the context of influenza viruses, there are two different standard approaches of antiviral treatment known: neuraminidase inhibitors and M2 protein inhibitors.

Accordingly, in one embodiment the virus is resistant to antiviral treatment. As outlined herein, the antiviral treatment may relate to the administration of neuraminidase inhibitors, such as oseltamivir, zanamivir, laninamivir and peramivir, and/or administration of M2 inhibitors such as amantadine and rimantadine. Accordingly, the antiviral treatment may be the administration of oseltamivir, zanamivir, amantadine and/or rimantadine. In another embodiment, the antiviral treatment relates to the administration of oseltamivir, zanamivir, peramivir, amantadine, rimantadine, favipiravir, baloxavir marboxil and/or pimodivir.

PD-0184264 can be used in a method for treating and/or prophylaxis of the medical conditions described herein. As such, the term "treating" or "treatment" includes administration of PD-0184264 preferably in the form of a medicament, to a subject suffering from a co-infection comprising a bacterial infection and a viral disease for the purpose of ameliorating or improving symptoms accompanying such infections. Similarly included is the administration of PD-0184264, preferably in the form of a medicament, to a subject suffering from a bacterial infection or for the purpose of ameliorating or improving symptoms accompanying such infections. Additionally included is the administration of PD-0184264, preferably in the form of a medicament, to a subject suffering from a viral infection or for the purpose of ameliorating or improving symptoms accompanying such infections. A co-infection comprising a bacterial infection and a viral disease, a viral disease and a bacterial infection is a medical condition treated or prevented by PD-0184264 or a pharmaceutically acceptable salt thereof.

Furthermore, the term "prophylaxis" or "prevention" as used interchangeably herein, refers to any medical or public health procedure whose purpose is to prevent a medical condition described herein. As used herein, the terms "prevent", "prevention" and "preventing" refer to the reduction in the risk of acquiring or developing a given condition, namely a coinfection comprising an viral infection and a bacterial infection, a bacterial infection alone or a viral infection alone as described herein. Also meant by "prophylaxis" is the reduction or inhibition of the recurrence of a co-infection comprising an influenza virus infection and a bacterial infection, a bacterial infection alone or a viral infection alone in a subject.

PD-0184264 of the present invention is effective in treating a coinfection as shown in Examples 3 and 8. A "coinfection" as used herein comprises a viral disease, preferably an influenza virus infection, and a bacterial infection. Such a coinfection can take place by simultaneous infection of a host e.g. a subject and/or single cell with a bacterium and influenza virus. It can also be that a host e.g. a subject and/or cell are simultaneously infected with one or more viral particles and one or more bacteria. However, such a coinfection can also take place sequentially. In such a case, a subject and/or cell is firstly infected with one or more viral particles and later in time the same subject and/or cell becomes infected with one or more bacteria or vice versa. The time period between the two infections can be a time period of at most 14 days, 13 days, 12 days, 11 days, 10 days, 9 days, 8 days, 7 days, 6 days, 5 days, 4 days, 3 days, 2 days, 1 day, 12 hours, 6 hours, 3 hours, 1.5 hours or at minimum 30 minutes. In this regard, due to the enlarged treatment window of PD-0184264, a more effective prevention of secondary bacterial infections is expected with extended administration.

Such a situation may also be a superinfection, in which a second infection is superimposed on an earlier one especially by a different microbial agent of exogenous or endogenous origin that is resistant to the treatment used against the first infection.

Within the influenza virus infection of the coinfection the influenza virus infection can be mediated by influenza A virus or influenza B virus, preferably the influenza A virus is H1N1, H2N2, H3N2, H5N6, H5N8, H6N1, H7N2, H7N7, H7N9, H9N2, H10N7, N10N8 or H5N1. In one embodiment, the influenza A virus is H1N1. In other embodiments, the influenza A virus is H3N2, H5N1 and H7N9. In additional embodiments, the influenza A virus is H3N2, H5N1, H1N1, H5N6, H7N2 and H7N9.

The present invention also relates to a "bacterial infection" which can take place in the setting of a coinfection described above present in a host, e.g. a subject and/or cell. The bacterial infection can be mediated by any bacterium; preferably it is mediated by a bacterium selected from the group consisting of Staphylococcaceae, Streptococcaceae, Legionellaceae, Pseudomonadaceae, Bacillaceae, Chlamydiaceae, Mycoplasmataceae, Enterobacteriaceae, Pseudomonadales and/or Pasteurellaceae.

The bacterial infection may be mediated by a bacterium selected from the group consisting of *Staphylococcus*, preferably *Staphylococcus aureus*, methicillin-sensitive and methicillin-resistant *Staphylococcus aureus*, Panton-Valentine leucocidin (PVL)-expressing *Staphylococcus aureus* and/or Streptococcaceae, preferably *Streptococcus mitis, Streptococcus pyogenes* or *Streptococcus pneumonia, Legionella*, preferably *Legionella pneumophila, Pseudomonas*, preferably *Pseudomonas aeruginosa, Bacillus*, preferably *Bacillus subtilis, Chlamydophila*, preferably *Chlamydophila* pneumonia, *Mycoplasma*, preferably *Mycoplasma* pneumonia, *Klebsiella*, preferably *Klebsiella* pneumonia, *Moraxella*, preferably *Moraxella catarrhalis* and/or *Haemophilus*, preferably *Haemophilus* influenza. Preferably the bacterium is selected from the group consisting of *Staphylococcus aureus, Streptococcus* pneumonia or *Haemophilus* influenza. Most preferably the bacterium is *Staphylococcus aureus*.

The "viral disease" or "viral infection" to which this invention also relates can take place in the setting of a coinfection described above or can occur as the only infection present in a host, e.g. a subject and/or cell. The viral disease or viral infection can be mediated by any virus; preferably it is mediated by a virus that causes respiratory tract infections such as an RNA virus. Preferred viruses are influenza viruses or corona viruses. Preferably, the influenza virus infection is mediated by influenza A or influenza B virus, wherein influenza A viruses are preferred. Particularly preferred are the influenza A virus subtypes H1N1, H2N2, H3N2, H5N6, H5N8, H6N1, H7N2, H7N7, H7N9, H9N2, H10N7, N10N8 and/or H5N1. Preferably, the corona virus infection is mediated by SARS-CoV, SARS-CoV2 or MERS-CoV.

In an alternate embodiment PD-0184264 is administered in combination with one or more MEK inhibitors. MEK inhibitors comprise e.g. U0126, PLX-4032, AZD6244, AZD8330, AS-703026, GSK-1120212, RDEA-119, RO-5126766, RO-4987655, CI-1040, PD-0325901, GDC-0973, TAK-733, PD98059, ARRY-438162, ARRY-162, ARRY-300, PF-3644022 and PD184352. The additional MEK inhibitor may be administered contemporaneously, previously or subsequently to PD-0184264.

Preferably, PD-0184264 is for use the methods for the prophylaxis and/or treatment of a co-infection of the present invention, wherein PD-0184264 is combined with one or more inhibitors targeting the influenza virus or the bacterium. PD-0184264 may be administered contemporaneously, previously or subsequently to the one or more inhibitors targeting the influenza virus.

In general, an inhibitor targeting the influenza virus is any inhibitor or medicament effective in influenza therapy. Different substances are known to be effective in reducing an influenza virus infection. Among them are for example inhibitors against the viral neuraminidase, compounds targeting a viral ion channel protein (M2) and compounds targeting viral polymerase or endonuclease activity via interfering with a component of the viral polymerase complex: PB1, PB2, PA or NP. By the invention also pharmaceutically acceptable salts of the inhibitors are envisioned. A preferred inhibitor, however, is a MEK inhibitor, particularly preferred PD-0184264, as described herein.

"MEK inhibitors" inhibit the mitogenic signaling cascade Raf/MEK/ERK in cells or in a subject by inhibiting the MEK (mitogen-activated protein kinase kinase). This signaling cascade is hijacked by many viruses, in particular influenza viruses, to boost viral replication. Specific blockade of the Raf/MEK/ERK pathway at the bottleneck MEK therefore impairs growth of viruses, in particular influenza viruses. Additionally, MEK inhibitors show low toxicity and little adverse side effects in humans. There is also no tendency to induce viral resistance (Ludwig, 2009). A particularly preferred inhibitor is PD-0184264.

A "neuraminidase inhibitor" is an antiviral drug targeted at influenza virus, which works by blocking the function of the viral neuraminidase protein, thus preventing virus from being released from the infected host cells, since the newly produced viruses cannot bud off from the cell in which they have replicated. Also comprised are pharmaceutically acceptable salts of a neuraminidase inhibitor. Preferred neuraminidase inhibitors are oseltamivir, zanamivir, peramivir, laninamivir or a pharmaceutically acceptable salt of any of these substances, such as oseltamivir phosphate, oseltamivir carboxylate, etc. Most preferred neuraminidase inhibitors are oseltamivir phosphate, zanamivir, oseltamivir or peramivir.

Compounds targeting the viral ion channel protein (M2) are for example amantadine and/or rimantadine, while compound targeting polymerase or endonuclease activity via interfering with a component of the viral polymerase complex, PB1, PB2, PA or NP are for example the NP blocker nucleozin or the polymerase inhibitor T-705 (Favipiravir).

Additionally, PD-0184264 can be combined with one or more inhibitors targeting the bacterium. Example 6 shows that PD-0184264 increases the sensitivity of bacteria to antibiotics. An inhibitor targeting the bacterium can be any inhibitor effective in reducing bacterial infection. In the present invention, PD-0184264 is strongly preferred as an inhibitor targeting the bacterium, but another inhibitor targeting the bacterium known to the skilled artesian is an antibiotic. Preferred antibiotics can be obtained from table 1 (FIG. 12). Thus, in one embodiment, the antibiotic is selected from the group consisting of the antibiotics as listed in table 1 (FIG. 12). In a further embodiment, the antibiotic is selected from the group consisting of the class of antibiotics as listed in table 1 (FIG. 12). In another embodiment, the antibiotic is selected from the group consisting of the generic name of the antibiotics as listed in table 1 (FIG. 12).

More preferred are antibiotics selected from Gentamicin, Rifampicin, Lysostaphin, Erythromycin, Levofloxacin, Vancomycin, Teicoplanin, Penicillin and Oxacillin.

The "subject", which may be treated by the inhibitors, in particular MEK inhibitors, or combinations of inhibitors of the present invention is preferably a vertebrate. In the context of the present invention the term "subject" includes an individual in need of a treatment of a co-infection as described herein or a bacterial or a viral infection alone. Preferably, the subject is a patient suffering from a co-infection or a bacterial or viral infection alone or being at a risk thereof. Preferably, the patient is a vertebrate, more preferably a mammal. Mammals include, but are not limited to, farm animals, sport animals, pets, primates, mice and rats. Preferably, a mammal is a human, horse, dog, cat, cow, pig, mouse, rat etc., particularly preferred, it is a human. In some embodiments, the subject is a human subject, which optionally is more than 1 year old and less than 14 years old, between the ages of 50 and 65, between the ages of 18 or 50, or older than 65 years of age. In other embodiments the subject is a human subject, which is selected from the group consisting of subjects who are at least 50 years old, subjects who reside in chronic care facilities, subjects who have chronic disorders of the pulmonary or cardiovascular system, subjects who required regular medical follow-up or hospitalization during the preceding year because of chronic metabolic diseases, renal dysfunction, hemoglobinopathies, or immunosuppression, subjects with less than 14 years of age, subjects between 6 months and 18 years of age who are receiving long-term aspirin therapy, and women who will be in the second or third trimester of pregnancy during the influenza season.

In the method of the invention, PD-0184264 may be administered orally, intravenously, intrapleurally, intramuscularly, topically or via inhalation. Preferably, PD-0184264 is administered via inhalation, topically or orally. In preferred embodiment, PD-0184264 is administered once daily in an oral dosage between 100 mg and 900 mg, preferably 600 mg, for 7 to 21 days.

Specifically, as described in Example 14, PD-0184264 was administered with a starting dose of 100 mg and up to three escalation steps in seven arms, following a single ascending dose/multiple ascending dose (SAD/MAD) regime. Administration scheme was one dose PD-0184264, escalating 100 mg to 900 mg (SAD), followed by seven doses PD-0184264, escalating 100 mg to 600 mg QD over seven days (MAD). Each dose cohort was considered to be safe by the Safety Review Committee (SRC), with release allowed for the next higher dose (up to SAD 900 mg and MAD 600 mg, respectively). The observed pharmacokinetic profile supports the intended once-daily regime for the further clinical development.

Only few adverse events in total and no serious adverse events were observed during the trial. PD-0184264 is thus considered to be safe and well tolerable. Pharmacokinetics exposure and determination of MEK inhibition were verified and confirm the maintenance of clinically relevant blood levels.

The present invention also envisages different compositions, preferably pharmaceutical compositions. The present invention relates to a composition comprising PD-0184264 for use in a method for the prophylaxis and/or treatment of a co-infection comprising a bacterial infection and a viral disease. The present invention similarly relates to a composition comprising PD-0184264 for use in a method for the prophylaxis and/or treatment of a bacterial infection and/or viral disease. Also provided for by the present invention is a composition comprising PD-0184264 and one or more inhibitors targeting the virus, in particular influenza virus, and/or the bacterium for use in a method for the prophylaxis and/or treatment of a co-infection comprising a bacterial infection and a viral infection, in particular influenza virus infection. In addition, the present invention relates to a composition comprising PD-0184264 and one or more inhibitors targeting the bacterium for use in a method for the prophylaxis and/or treatment of a bacterial infection or viral infection.

As mentioned above, the composition comprising PD-0184264 and eventually one or more inhibitors targeting the bacterium and/or one or more inhibitors targeting the virus, in particular influenza virus, may be a pharmaceutical composition. A preferred embodiment of the pharmaceutical composition comprises PD-0184264 and an inhibitor targeting the influenza virus, in particular a neuraminidase inhibitor. In another embodiment, the pharmaceutical composition comprises PD-0184264 and a further MEK inhibitor. Preferably, such compositions further comprise a carrier, preferably a pharmaceutically acceptable carrier. The composition can be in the form of orally administrable suspensions or tablets, nasal sprays, preparations for inhalation devices, sterile injectable preparations (intravenously, intrapleurally, intramuscularly), for example, as sterile injectable aqueous or oleaginous suspensions or suppositories.

The pharmaceutical composition for the use of the invention and comprising PD-0184264 and optionally one or more inhibitors targeting an influenza virus and/or one or more inhibitors targeting a bacterium is administered to a patient which is a mammal or bird. Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human, with a human being preferred. Examples of suitable birds include, but are not limited to, a turkey, a chicken, a goose, a duck, a teal, a mallard, a starling, a Northern pintail, a gull, a swan, Guinea fowl or water fowl to name a few. Human patients are a particular embodiment of the present invention.

The inhibitor or inhibitors are preferably administered in a therapeutically effective amount. The "therapeutically effective amount" for PD-0184264 or each active compound/inhibitor can vary with factors including but not limited to the activity of the compound used, stability of the active compound in the patient's body, the severity of the conditions to be alleviated, the total weight of the patient treated, the route of administration, the ease of absorption, distribution, and excretion of the compound by the body, the age and sensitivity of the patient to be treated, adverse events, and the like, as will be apparent to a skilled artisan. The amount of administration can be adjusted as the various factors change over time.

The inhibitors, methods and uses described herein are applicable to both human therapy and veterinary applications. The compounds described herein, in particular, PD-0184264 and optionally one or more inhibitors targeting an influenza virus and/or one or more inhibitors targeting a bacterium having the desired therapeutic activity may be administered in a physiologically acceptable carrier to a subject, as described herein. Depending upon the manner of introduction, the compounds may be formulated in a variety of ways as discussed below. The concentration of therapeutically active compound in the formulation may vary from about 0.1-100 wt. %. The agents may be administered alone or in combination with other treatments. Example 1 shows that 25 and 75 mg/kg of PD-0184264 are effective in vivo by oral administration. Accordingly, the PD-0184264 may be administered at a dosage in the range of 10 to 100 mg/kg PD-0184264, preferably in the range of 25 to 75 mg/kg PD-0184264. Preferred administration is as a once daily dosage between 100 and 900 mg, including any dosage amount in between such as 200, 300, 400, 500, 600, 700, and 800 mg. In a preferred embodiment, administration is once daily and the dosage is 600 mg administered orally. PD-0184264 can be administered for a time period of 1 to 21 consecutive days or more, preferably for 7 to 14 days.

The pharmaceutical compounds in the method of present invention can be administered in any suitable unit dosage form. Suitable oral formulations can be in the form of tablets, capsules, suspension, syrup, chewing gum, wafer, elixir, and the like. Pharmaceutically acceptable carriers such as binders, excipients, lubricants, and sweetening or flavoring agents can be included in the oral pharmaceutical compositions. If desired, conventional agents for modifying tastes, colors, and shapes of the special forms can also be included.

For injectable formulations, the pharmaceutical compositions can be in lyophilized powder in admixture with suitable excipients in a suitable vial or tube. Before use in the clinic, the drugs may be reconstituted by dissolving the lyophilized powder in a suitable solvent system for form a composition suitable for intravenous or intramuscular injection.

The combination of PD-0184264 with an antiviral agent such as a neuraminidase inhibitor, such as oseltamivir, leads to a synergistic effect. This synergistic effect may be an increased antiviral effect resulting e.g. in a reduced virus titer or a prolonged therapeutic window. Accordingly, the present invention also relates to a pharmaceutical composition comprising a therapeutically effective amount of PD-0184264 as well as a therapeutically effective amount of a neuraminidase inhibitor chosen from the group of oseltamivir, oseltamivir phosphate, laninamivir, zanamivir and peramivir.

In one embodiment, the composition can be in an orally administrable form (e.g., tablet or capsule or syrup etc.) with a therapeutically effective amount (e.g., from 0.1 mg to 2000 mg, 0.1 mg to 1000 mg, 0.1 mg to 500 mg, 0.1 mg to 500 mg, 0.1 mg to 200 mg, 30 mg to 300 mg, 0.1 mg to 75 mg, 0.1 mg to 30 mg) of neuraminidase inhibitor as described above.

In further embodiments, PD-0184264 is for use in the methods for the prophylaxis and/or treatment of a co-infection of the present invention, wherein PD-0184264 reduces both the viral and bacterial infection, when contacting it with an in vitro test system, wherein the test system comprises cultured cells infected with
 a) an influenza virus
 b) a bacterium
when compared to the in vitro test system before contacting. In another embodiment, PD-0184264 is for use in the methods for the prophylaxis and/or treatment of a bacterial infection of the present invention, wherein PD-0184264 reduces the bacterial infection, when contacting it with an in vitro test system, wherein the test system comprises cultured cells infected with a bacterium, when compared to the in vitro test system before the contacting.

As such the present invention also relates to an in vitro test system, wherein the test system comprises cultured cells infected with
 a) an influenza virus and
 b) a bacterium.

Along this line, the present invention also provides for an in vitro test system, wherein the in vitro test system comprises cultured cells infected with a bacterium.

In the cases where the in vitro test system includes a viral and bacterial infection, again, these infections can be taking place sequentially or simultaneously.

A "cultured cell" or "cultured cells" is/are cells, which are not present in their natural environment e.g. within a plant or animal. Rather a cultured cell may be a primary cell culture, which comprises cells isolated from their natural environment, or a cell line. Preferably the cultured cells are human lung epithelial cells. Preferably, the cultured cells are seeded at a density of about $1\times10^5$, $2\times10^5$, $3\times10^5$, $4\times10^5$, $5\times10^5$, $6\times10^5$, $7\times10^5$, $8\times10^5$, $9\times10^5$, $10\times10^5$, $11\times10^5$, most preferably $8\times10^5$ cells in 0.5 ml, 1 ml, 1.5 ml, 2 ml, 2.5 ml, 3 ml, 3.5 ml, 4 ml medium such as DMEM. Most preferred is a density of $8\times10^5$ in 2 ml DMEM.

Such cultured cells are infected with a virus and a bacterium or in other embodiments with a bacterium alone. As already described above, a co-infection can take place in a sequential or simultaneous manner. For example, the cultured cells may be infected first with the influenza virus and 30 minutes later with bacterium/bacteria. It is also possible to additionally add an antibiotic to the culture after 3 hours, to remove extracellular bacteria. In such a scenario the antibiotic would then become washed off again. In other embodiments, the cells are only infected with a bacterium.

The term "contacting" as used herein refers to the bringing of a cell comprising an influenza virus and a bacterium spatially into close proximity to PD-0184264. This can for example mean that an inhibitor is applied to the medium in which the cultured cells are located via a syringe.

In one embodiment, the reduction of the viral infection is a reduction in plaque forming units (PFU)/ml and the reduction in the bacterial infection is a reduction in colony forming units (CFU)/ml.

The "plaque forming units" is a measure of the number of particles capable of forming plaques per unit volume, such as virus particles. It is a functional measurement rather than a measurement of the absolute quantity of particles: viral particles that are defective or which fail to infect their target cell will not produce a plaque and thus will not be counted. For example, a solution of influenza virus with a concentration of 1,000 PFU/µl indicates that 1 µl of the solution carries enough virus particles to produce 1000 infectious plaques in a cell monolayer. In the case of the present invention, a cell culture treated with an inhibitor shows a reduced number of plaque forming units in a culture after the treatment, when compared to a culture before the treatment with PD-0184264.

A possible "reduction in plaque forming units (PFU)/ml" is analyzed in the following way. First the cultured cells, which are co-infected with an influenza virus and a bacterium, are analyzed for their ability to generate plaque forming units (PFU)/ml by e.g. sucking of some cells from the Petri dish and plating them for counting the bacterial plaques that will form. This result is then compared to the number of plaque forming units (PFU)/ml generated by cells of the same culture after the inhibitor was applied. If the number of the plaque forming units (PFU)/ml is reduced after the treatment with an inhibitor compared to the number generated before the application of the inhibitor, there is a reduction in the plaque forming units.

The "colony forming units (CFU)/ml" estimates the number of viable bacteria in a sample. Different methods exist. For example, to generate colony forming units a sample (e.g. cultured cells in a small volume) is spread across the surface of a nutrient agar plate and allowed to dry before incubation for counting. A viable bacterium is defined as the ability to multiply via binary fission under the controlled conditions. The visual appearance of a colony in a cell culture requires significant growth—when counting colonies it is uncertain if the colony arose from one cell or 1,000 cells. Therefore, results are reported as CFU/ml (colony-forming units per milliliter) for liquids and CFU/g (colony-forming units per gram) for solids to reflect this uncertainty (rather than cells/ml or cells/g).

"Colony forming units (CFU)/ml" can be analyzed in the following way. First the cultured cells, which are co-infected with an influenza virus and a bacterium or with a bacterium alone, are analyzed for their ability to generate colony forming units (CFU)/ml by e.g. sucking of some cells from the Petri dish and plating them for counting. This result is then compared to the number of colony forming units (CFU)/ml generated by cells of the same culture after the inhibitor was applied. If the number of the colony forming units (CFU)/ml is reduced to the number generated before the application of the inhibitor, there is a reduction.

In general, the person skilled in the art knows these well-known techniques of analyzing bacterial and viral infections. How one can measure the plaque forming units (PFU)/ml and the colony forming units (CFU)/ml is further described in the literature (Tuchscherr et al. 2011, Hrincius et al. 2010).

For the purpose of the invention the active compound as defined above also includes the pharmaceutically acceptable salt(s) thereof. The phrase "pharmaceutically or cosmetically acceptable salt(s)", as used herein, means those salts of compounds of the invention that are safe and effective for the desired administration form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, etc.

The invention is also characterized by the following items:

1. PD-0184264 or a pharmaceutically acceptable salt thereof for use in a method for the prophylaxis and/or treatment of a viral disease.
2. PD-0184264 or a pharmaceutically acceptable salt thereof for the use according to item 1, wherein the virus is a negative strand RNA virus.
3. PD-0184264 or a pharmaceutically acceptable salt thereof for the use according to item 1 or 2, wherein the virus is influenza virus.
4. PD-0184264 or a pharmaceutically acceptable salt thereof for the use according to any one of items 1-3, wherein the influenza virus is influenza A virus or influenza B virus.
5. PD-0184264 or a pharmaceutically acceptable salt thereof for use in a method for the prophylaxis and/or treatment of a bacterial infection.
6. PD-0184264 or a pharmaceutically acceptable salt thereof for the use according to item 5, wherein the bacterial infection is mediated by a bacterium selected from the group consisting of Staphylococcaceae, Streptococcaceae, Legionellaceae, Pseudomonadaceae, Bacillaceae, Chlamydiaceae, Mycoplasmataceae, Enterobacteriaceae, Pseudomonadales and/or Pasteurellaceae.
7. PD-0184264 or a pharmaceutically acceptable salt thereof for use in a method for the prophylaxis and/or treatment of a co-infection comprising a bacterial infection and a viral disease.
8. PD-0184264 or pharmaceutically acceptable salt thereof for the use according to item 7 wherein the bacterial infection is mediated by a bacterium selected from the group consisting of Staphylococcaceae, Streptococcaceae, Legionellaceae, Pseudomonadaceae, Bacillaceae, Chlamydiaceae, Mycoplasmataceae, Enterobacteriaceae, Pseudomonadales and/or Pasteurellaceae.
9. PD-0184264 or a pharmaceutically acceptable salt thereof for the use according to item 7 or 8, wherein the virus is a negative strand RNA virus.
10. PD-0184264 or a pharmaceutically acceptable salt thereof for the use according to any one of items 7-9, wherein the viral infection is caused by an influenza virus.
11. PD-0184264 or a pharmaceutically acceptable salt thereof for the use according to any one of items 7-10, wherein in the viral infection is caused by influenza A virus or influenza B virus.
12. PD-0184264 or a pharmaceutically acceptable salt thereof for the use according to any one of items 1-4 and 7-11, wherein PD-0184264 or a pharmaceutically acceptable salt thereof is administered in combination with a neuraminidase inhibitor or a pharmaceutically acceptable salt thereof.
13. PD-0184264 or a pharmaceutically acceptable salt thereof for the use according to item 12, wherein the neuraminidase inhibitor is selected from oseltamivir, oseltamivir phosphate, zanamivir, laninamivir or peramivir or a pharmaceutically acceptable salt thereof.
14. A pharmaceutical composition comprising PD-0184264 or a pharmaceutically acceptable salt thereof.
15. A pharmaceutical composition comprising PD-0184264 or a pharmaceutically acceptable salt thereof and a neuraminidase inhibitor or a pharmaceutically acceptable salt thereof.
16. Any use of the preceding items comprising a further MEK inhibitor.
17. PD-0184264 or a pharmaceutically acceptable salt thereof for the use according to any one of the preceding items in a subject, preferably a vertebrate.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

EXAMPLES

The following examples illustrate the invention. These examples should not be construed as to limit the scope of the invention. The examples are included for purposes of illustration and the present invention is limited only by the claims.

Example 1: Treatment of Mice with PD-0184264 Leads to Reduction of Virus Titer in the Lung 8 weeks old C57BL/6 mice (five per group) were infected with $1.5 \times 10^5$ PFU ($5 \times MLD_{50}$) of the influenza virus strain A/Regensburg/D6/2009, (RB1, H1N1pdm09). Starting one hour prior to the infection mice were treated with either 150 mg/kg CI-1040; 75 mg/kg CI-1040, 25 mg/kg CI-1040, 75 mg/kg PD0184264, 25 mg/kg PD0184264 or solvent (control): 50 µl DMSO/150 µl Cremophor/800 µl PBS in an 8 h interval. All animals received a volume of 200 µl per os. Mice were sacrificed 24 h post infection and lungs were weighed, transferred into a Lysing Matrix D tube (MP Bio) and BSS (buffered salt solution) in an amount of the 10-fold volume of the lung was applied to the samples. Organs were shredded using the FastPrep FP 120 (Savant). To remove the cell debris the homogenates were centrifuged for 15 min at 2000 rpm and the supernatant collected. The determination of virus titer in homogenates was performed using the AVICEL® plaque assay. Results are presented in FIG. 1 as virus titer (log 10) pfu/ml (left) or % virus titer (right). Virus titer was determined by two investigators independently. Mean values from all titrations were presented.

Example 2: Administration of CI-1040 or PD-0184264 Exhibit Inhibitory Effects on Bacterial Growth Including MRSA In Vitro To investigate the effect of CI-1040 or PD-0184264 on bacteria growth in general, a cell-free over-night culture of MRSA strain S. aureus (USA300) was supplemented with 50 µM of either CI-1040 or PD-0184264 or the same volume (40 µl) of DMSO, serving as a solvent (FIG. 2). Bacterial growth was monitored for 360 minutes. PD-0184264 had a strong impact on bacterial growth, which was almost complete absent over the whole observation period. CI-1040 slightly inhibited growths of MRSA starting 120 min after onset of the experiment, in comparison to the solvent control as can be seen from FIG. 2. This indicates that PD-0184264 but also CI-1040 in addition to blocking MEK in cells also blocks a bacterial component responsible for bacterial growth.

For investigation of the concentrations of PD-0184264 needed to inhibit bacterial growth, PD-0184264 was administrated in different concentrations (as indicated in FIG. 3) to an over-night culture of S. aureus USA300 (MRSA). MRSA bacteria were incubated with different concentrations of the MEK inhibitor ranging from 0-100 µM and bacterial growth was monitored six hours after cultivation. The concentration needed to inhibit 50% of bacterial growths was in the range of 15-25 µM.

These data could be verified in a slightly different experimental setting, determining actual bacterial titers instead of OD at later time points post treatment. An over-day culture of S. aureus 6850 was set to 20 CFU/ml and treated with different concentrations of CI-1040 as indicated over night at 37° C. and 5% $CO_2$. Then, the optical density ($OD_{600}$) was measured. The remaining culture was washed with PBS and serial dilutions were objected to BHI agar plates. Bacterial titers are shown as colony forming units per ml (CFU/ml). Results represent means+SD of three independent biological experiments with two technical replicates are shown in FIG. 4A. In addition, over-day cultures of S. aureus 6850 (FIG. 4B) or the MRSA strain USA300 (FIG. 4C) were set to 20 CFU/ml and treated with different concentrations of PD-0184264 as indicated over night at 37° C. and 5% $CO_2$. In the morning, the optical density (OD600) was measured. The remaining cultures were washed once with PBS and serial dilutions were then objected to BHI agar plates. Bacterial titers were determined using colony counter "protocol3" and are shown as colony forming units per ml (CFU/ml) in a logarithmic scale. Results represent means±SD of three independent biological experiments with two technical replicates. Statistical significance was analyzed by one-way ANOVA followed by Dunnett's multiple comparisons test. Both, CI-1040 (FIG. 4A) and PD-0184264 (FIG. 4B, C) were also effective in these assays against S. aureus strain 6850 (FIGS. 4A, B) and MRSA strain USA 300 (FIG. 4C) A very strong reduction of titers up to 1.5-2 orders of a magnitude could be detected with 20 µM of PD-0184264 (FIG. 4B, C).

Example 3: Administration of PD-0184264 to Singular or Co-Infected Cells Protects Cells from Cytopathic Effects of IAV and/or S. aureus Given the antiviral and the strong antibacterial effect of PD-0184264 (FIG. 2 to 4 in Example 2 above) we analyzed whether this feature of the compound could also be observed macroscopically with regard to the cell disrupting cytopathic effects (CPE) elicited by IAV (influenza A virus) and/or S. aureus infection. Human lung epithelial cells (A549) were pretreated with PD-0184264 (at the concentrations indicated) or solvent (DMSO) and infected with human influenza virus strain A/Puerto Rico/8/34 (H1N1) at a multiplicity of infection (MOI=0.001) at 37° C. After 30 min the virus dilution was removed, cells were rinsed with PBS and supplemented with invasion medium DMEM/INV (containing 1% human serum albumin, 25 nM HEPES) with or without S. aureus 6850 (MOI=0.1) in presence of the indicated concentrations of the inhibitor or solvent control. 3 h post bacterial infection cells were treated with DMEM/FBS containing 10% FBS, 2 µg/ml lysostaphin for 20 min to remove extracellular bacteria. After an additional wash with PBS, cells were supplemented with infection medium DMEM/BA (0.2% BA, 1 mM MgCl2, 0.9 mM CaCl2, 100

U/ml penicillin, 0.1 mg/ml streptomycin) containing inhibitor or solvent. After an incubation period of 24 h at 37° C., cell morphology was examined by light microscopy. As shown in FIG. 5, a slight disruption of the cell monolayer was observed following singular infection with IAV (H1N1) or the *S. aureus* strain 6850. This CPE was strongly increased upon co-infection with both pathogens (lower panel). However, with increasing amounts of the MEK-inhibitor this phenotype could be reversed in a concentration dependent manner as the cell monolayer stayed intact and cells were less round shaped. This cell protective effect of PD-0184264 perfectly reflects its antiviral and anti-bacterial properties (FIG. 5).

Example 4: Comparison of the Antibacterial Action of PD-0184264 to the Common Antibiotics To align the antibacterial properties of the MEK-inhibitor PD0184164 with the action of a common antibiotic, we treated bacteria over-night with solvent, the MEK-inhibitors U0126 and PD-0184264 or different concentrations of the antibiotic gentamicin. Over-day cultures of *S. aureus* 6850 or the MRSA strain USA300 were set to 20 CFU/ml and treated as indicated over night with either MEK inhibitors U0126 and PD-0184264 or the antibiotic Gentamicin at 37° C. and 5% $CO_2$. In the morning, the optical density (OD600) was measured. The remaining cultures were washed once with PBS and serial dilutions were then objected to BHI agar plates. Bacterial titers were determined using colony counter "protocol3" and are shown as colony forming units per ml (CFU/ml). Results shown in FIG. 6 represent means±SD of three independent biological experiments with two technical replicates.

Statistical significance was analyzed by one-way ANOVA followed by Dunnett's multiple comparisons test. In comparison with the solvent treated bacteria, incubation with the first generation MEK-inhibitor U0126 resulted only in a minor reduction in bacterial titers, whereas treatment with PD-0184264 led to a very strong reduction in bacterial load as shown before in FIG. 4. This was true for both bacterial strains. As expected, the growth of both bacterial strains was strongly inhibited by gentamicin treatment with concentrations higher than 1 µg/ml, although the antibacterial action of the antibiotic was higher in case of *S. aureus* 6850. At 0.5 µg/ml gentamicin no reduction in bacterial titers could be detected for both strains. In summary, the impact of the MEK-inhibitor PD-0184264 on bacterial growth was almost as efficient as low concentrations of the antibiotic gentamicin.

To further compare the antibacterial action of the PD-0184264 with other MEK-inhibiting compounds or the antibiotic gentamycin, time-of-addition assays were performed (FIG. 7a). An over-night culture of *S. aureus* 6850 was divided into six subcultures containing 15 ml of BHI medium together with the solvent DMSO alone or with one of the MEK-inhibitors U0126 and PD-0184264 or two different concentrations of the antibiotic gentamicin (0.5 or 2 µg/ml). Immediately after the addition of the different compounds the OD600 was measured and serial dilutions were objected to BHI agar plates to calculate bacterial titers. The remaining cultures were further incubated at 37° C. with 5% $CO_2$ in the presence of the substances or solvent alone. This procedure was repeated two times at 3 h and 6 h post inoculation. Bacterial titers were determined using colony counter "protocol3" and are shown as colony forming units per ml (CFU/ml). Treatment with the MEK-inhibitor PD-0184264 showed the strongest inhibition of bacterial growth compared with all other compounds. Afterwards, a medium exchange was performed and the cultures were further incubated without addition of any substances. All cultures reached the turbidity of the previously solvent treated culture, which indicates that the MEK inhibitor PD-0184264 exhibits a bacteriostatic rather than a bactericidal action.

Resistance development against a variety of commonly used antibiotics regularly occurs and represents a major problem in the clinics. To test whether the MEK inhibitor PD0184264 causes resistance development in *S. aureus*, cultures were constantly treated for almost three weeks in the presence of either the inhibitor, Gentamicin, Erythromycin or were left untreated. Specifically, cultures were grown for 24 h in the presence or absence of the substances, the $OD_{600}$ was measured and then cultures were set to 20 CFU/ml and grown again for 24 h. This procedure was repeated for 17 days. Data represent means+SD of three independent experiments. Statistical significance was analyzed by one-way ANOVA followed by Dunnett's multiple comparisons test (* $p<0.05$;  $p<0.01$; * $p<0.001$; **** $p<0.0001$). As seen for Gentamicin, resistance development occurred during the first week of treatment in contrast to the macrolide antibiotic Erythromycin. Notably, the treatment with the MEK inhibitor did not induce resistance (See the results shown in FIG. 7b).

Example 5: The Bacterial Kinase PknB May be a Target of PD-0184264 in Bacteria

Figure 8:
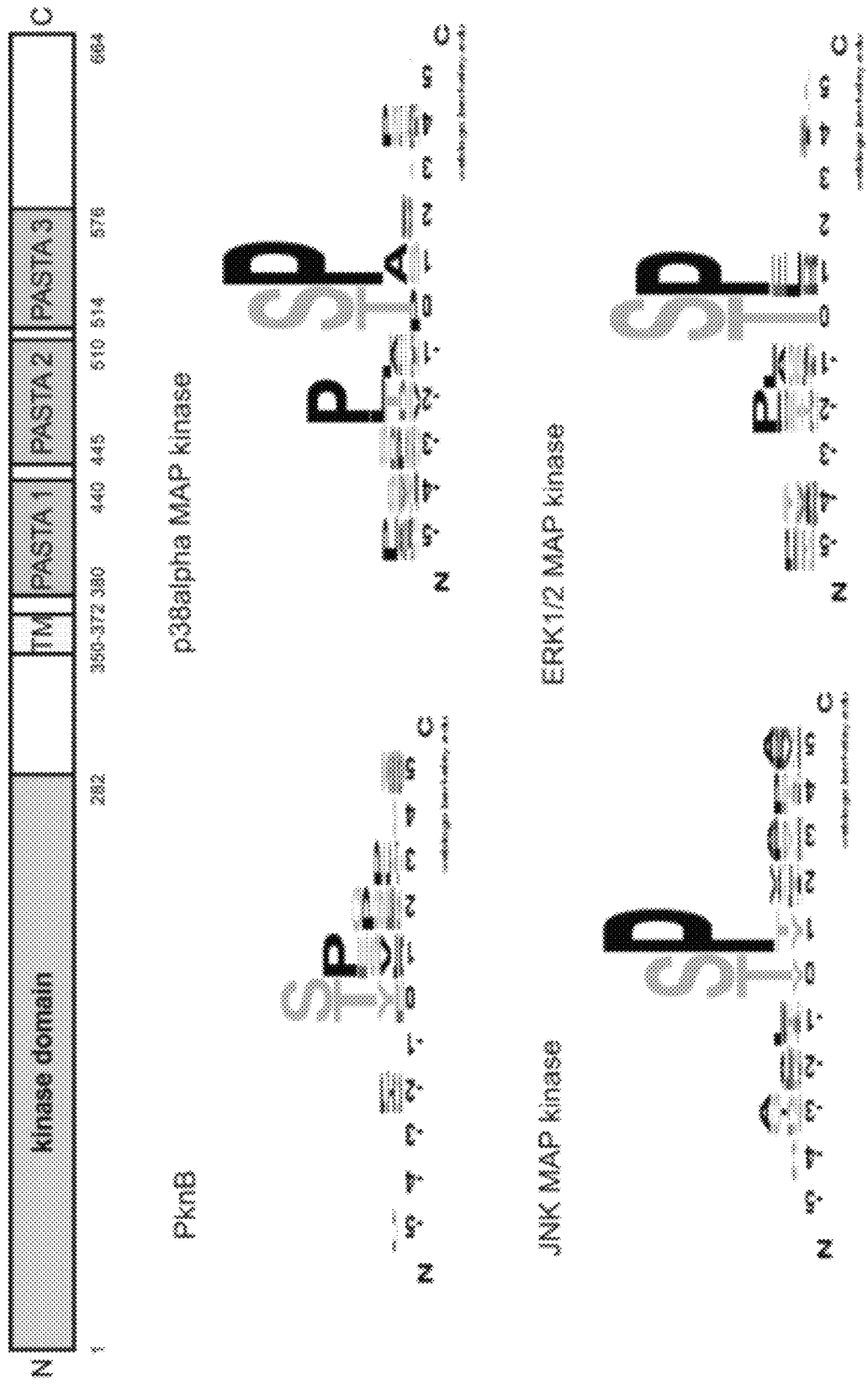
FIG. 8: Domain structure of the bacterial kinase PknB (top) (Rakette et al. 2012) and sequence homologies of the auto-phosphorylation site of PknB with the activation sites of mammalian MAP kinases p38, JNK, and the direct MEK target ERK (Miller et al. 2010).

The inhibitor PD-0184264 is supposed to be specific for the kinase MEK that exists in mammals. Its direct antibacterial effect raises the question about the mode of action in prokaryotes, i.e. is there a MEK-like bacterial component, which could also be specifically targeted by the PD-0184264. At this point, the bacterial serine/threonine kinase PknB came into the focus of investigation. This kinase shows high structural and functional similarity to cellular serine/threonine kinases, more precisely to MAP kinases such as p38, JNK and ERK (Miller et al., 2010, Rakette et al. 2012) (FIG. 8), that are MEK-targets in mammalian cells. Interestingly the kinase was shown to be activated by autophosphorylation, thus, strongly suggesting that it exhibits a MEK-like activity.

Example 6: PD-0184264 Increases the Sensitivity of *Staphylococcus aureus* to Antibiotics and Reduces Bacterial Stress Resistance Due to the expression of three penicillin binding domains (PASTA) (see FIG. 8, upper panel) PknB is involved in the regulation of antibiotic susceptibility. It could be shown that a lack of the kinase results in increased susceptibility to different antibiotics, especially a variety of β-lactams (Tamber et al. 2010). To investigate if the treatment of bacteria with the MEK-inhibitor PD-0184264 may have an impact on the bacterial kinase and results in a similar phenotype as knock-out of the kinase, bacterial cultures were treated over night with solvent (DMSO) or 20 µM of PD-0184264 and were then used to determine the minimal inhibitory concentration (MIC) of different antibiotics. Over-day cultures of *S. aureus* 6850 were set to 20 CFU/ml and treated with either solvent (DMSO or the MEK-inhibitor PD-0184264 over night at 37° C. and 5% $CO_2$. In the morning, the optical density (OD600) was measured. Briefly, solvent and inhibitor treated cultures were washed once with PBS and 1:1 dilutions were objected to BHI agar plates. Shortly after inoculation MIC test stripes for different antibiotics (Thermo Fischer Scientific) were placed in the middle of the plate and were then incubated for 18 to 24 h at 37° C. After 18 h incubation at 37° C. the MIC concentrations were determined via visual analysis of the plates. The concentration, at which no growth inhibition was visible any more, was termed as the MIC for each individual antibiotic. Treatment with the PD-0184264 indeed led to an increase in susceptibility of the bacteria to different antibiotics, which was most prominent in case of penicillin and gentamicin (FIG. 9, Table 2). This result is in perfect agreement to published data generated with the mutant strain, which lacks the kinase (Tamber et al. 2010).

TABLE 2

Determination of MICs after over-night treatment with PD0184264

| | Minimal inhibitory concentration (MIC) [mg/L] | | | |
|---|---|---|---|---|
| | S. aureus 6850 | | S. aureus USA300 | |
| | untreated | PD0184264 | untreated | PD0184264 |
| Penicillin | 16 | 0.25-0.5 | >256 | 8 |
| Meropenem | 0.06 | 0.03 | 0.12-0.25 | 0.06 |
| Linezolid | 2 | 1 | 2 | 1 |
| Ciprofloxacin | 0.25 | 0.12-0.25 | 8 | 4-8 |
| Gentamicin | 2 | 0.12 | 1 | 0.12 |

The observed increase in antibiotic susceptibility upon treatment with PD-0184264, which matches the phenotype of bacteria that are lacking the kinase (Tamber et al. 2010), strongly suggests that PknB might be directly targeted by the inhibitor. As the kinase is known to play an important role in bacterial stress resistance, bacterial growth under heat stress was monitored after treatment of the bacteria with the inhibitor PD-0184264. S. aureus strain 6850 and MRSA strain USA300 were treated over night with either solvent or 20 µM of the PD-0184264. The next day subcultures with the same amount of bacteria were prepared (confirmed by OD600 and plating on BHI agar) and further incubated at 42° C. for 6 h. Bacterial titers were then calculated via plating of serial dilutions on BHI agar plates. As shown in FIG. 10, PD-0184264-treated bacteria were strongly impaired under these conditions compared to solvent treated pathogens. This is both observed for the methicillin-sensitive strain 6850 (black bars) as well as for the MRSA strain USA300 (grey bars). Impaired stress tolerance in the presence of the inhibitor is another indication that PD-0184264 directly targets the kinase PknB, which is an important mediator of stress resistance. In summary, the data provide strong circumstantial evidence, that PD-0184264 elicits its antibacterial action by inhibition of the bacterial kinase PknB.

Example 7: Administration of PD-0184264 Exhibits Inhibitory Effects on Growth of *Streptococcus pneumoniae* and *Bacillus subtilis*

Beside S. aureus, there are other bacteria known to cause secondary bacterial pneumonia following influenza virus (IV) infections in patients. The most abundant pathogen in this context is *Streptococcus pneumoniae*. These bacteria represent the most common cause for community-acquired pneumonia. In contrast to S. aureus, secondary infections with *Streptococcus pneumoniae* occur rather in a late phase following IV and therefore correspond to the terminus post-influenza pneumonia.

Similar to S. aureus, the majority of *Streptococcus pneumoniae* strains express eukaryotic-like serine/threonine kinases, such as PknB, which are highly conserved between different genera.

Additionally, these kinases share high homology to cellular MAP kinases (e.g. ERK, JNK, p38). Results shown in examples 2-6 gained with different S. aureus strains already demonstrated an inhibitory effect of PD-0184264 treatment on bacterial growth, which pointed towards the involvement of bacterial kinases, such as PknB in the observed phenotype. Strikingly, a homolog of S. aureus PknB also exists in *Streptococcus* pneumonia, suggesting that these bacteria may also be sensitive to PD-0184264. Thus, the impact of PD-0184264 on different strains of Streptococci pneumonia was analyzed. *Streptococcus pneumoniae* strains can be divided into different serotypes, which differ in their virulence and overall pathogenicity. To test for a serotype- or strain-independent effect, we used the encapsulated strains D39 and TIGR4, which are both virulent, but belong to different serotypes. It was found that treatment with PD-0184264 impairs growth of different serotypes of *Streptococcus pneumoniae*. Specifically, over-day cultures of *Streptococcus pneumoniae* strains TIGR4 (serotype 4) and D39 wt (serotype 2) were set to an optical density (OD600) of 1, diluted 1:2000 in BHI medium and treated over night with solvent (DMSO) or different concentrations of the specific MEK inhibitor PD0184264 (PD; active metabolite of CI-1040) as indicated. Then, the OD600 was measured again (Results shown in FIG. 11A) and dilution series were objected to BHI agar plates to determine bacterial titers (Results shown in FIG. 11B). As a result, it could be demonstrated that both serotypes are sensitive to PD-0184264 (FIG. 11 a, b).

Figure 11:
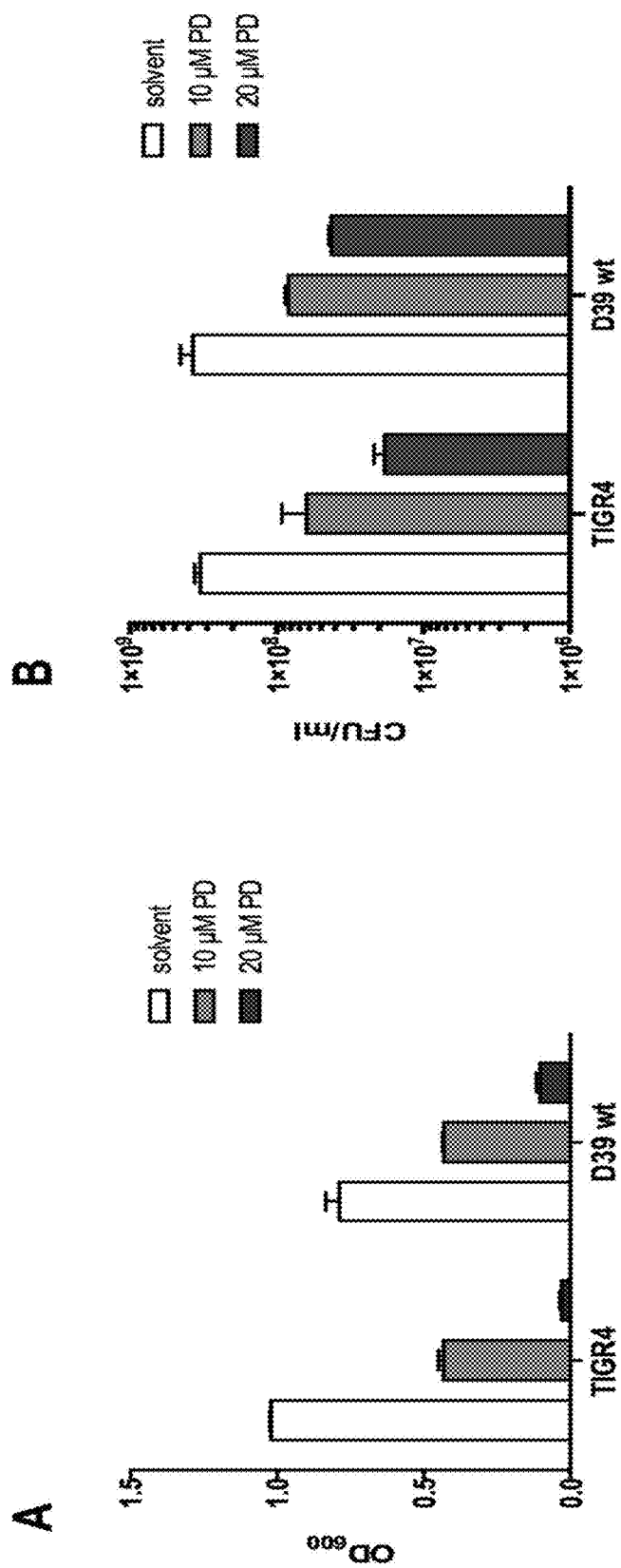
FIG. 11: Treatment with PD-0184264 impairs growth of different serotypes of Streptococcus pneumoniae.
(A) Effect of PD-0184264 on cultures of Streptococcus pneumoniae strains TIGR4 (serotype 4) and D39 wt (serotype 2) as measured by OD600; (B) Effect of PD-0184264 on cultures of Streptococcus pneumoniae strains TIGR4 (serotype 4) and D39 wt (serotype 2) shown in CFU/ml; (C): Effect of PD-0184264 on cultures of Bacillus subtilis shown in CFU/ml.
Figure 11:
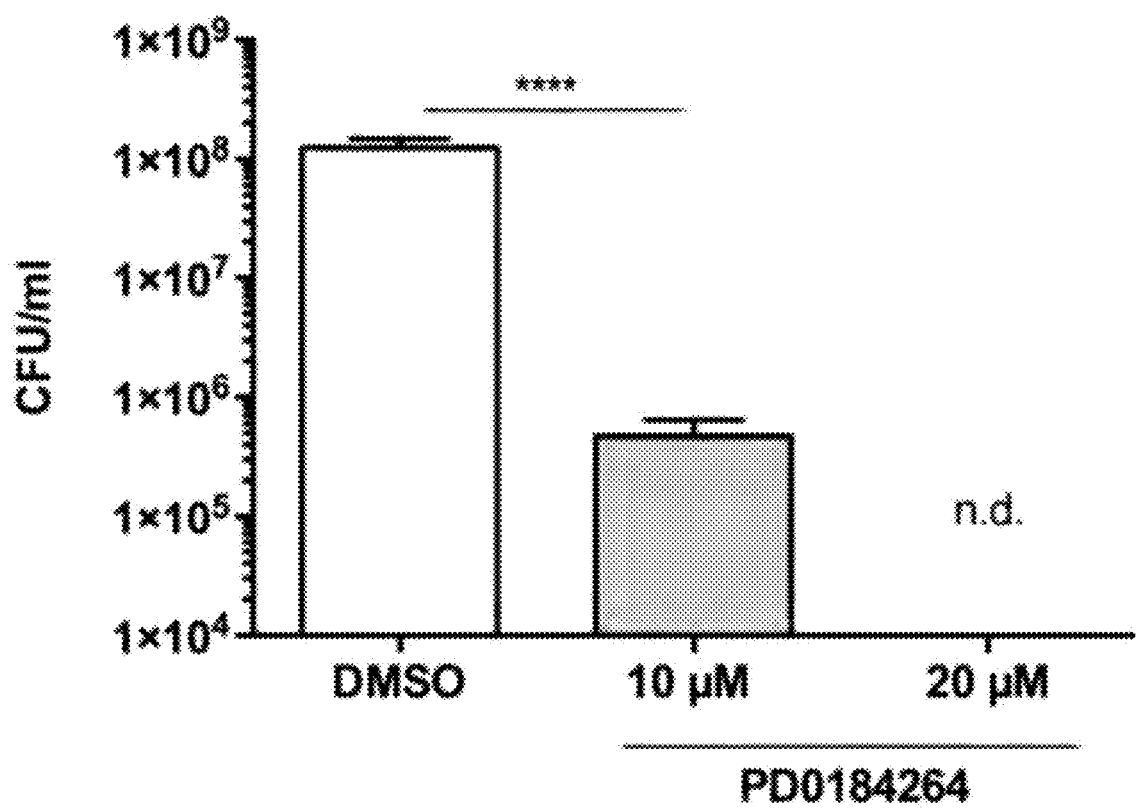

The same is true for *Bacillus subtilis*, for which also a strong decrease in viable bacterial counts was observed in the presence of 10 µM PD-0184264 and complete abolishment at higher concentrations (see results in FIG. 11 c). Specifically, to test for a potential antibacterial effect on B. subtilis, over-night cultures of B. subtilis were incubated with either solvent or different concentrations of the MEK inhibitor PD-0184264 (as indicated) for 18 h. Afterwards, bacterial load was determined via measurement of the OD600 and plating of serial dilutions on BHI agar plates. Data shown in FIG. 11 represent means+SD of three independent experiments.

In sum, these data indicate a broad applicability of PD-0184264 in antibacterial treatments.

Example 8: PD-0184264 but not CI-1040 Decreases Intracellular Bacterial Titers

Figure 13:
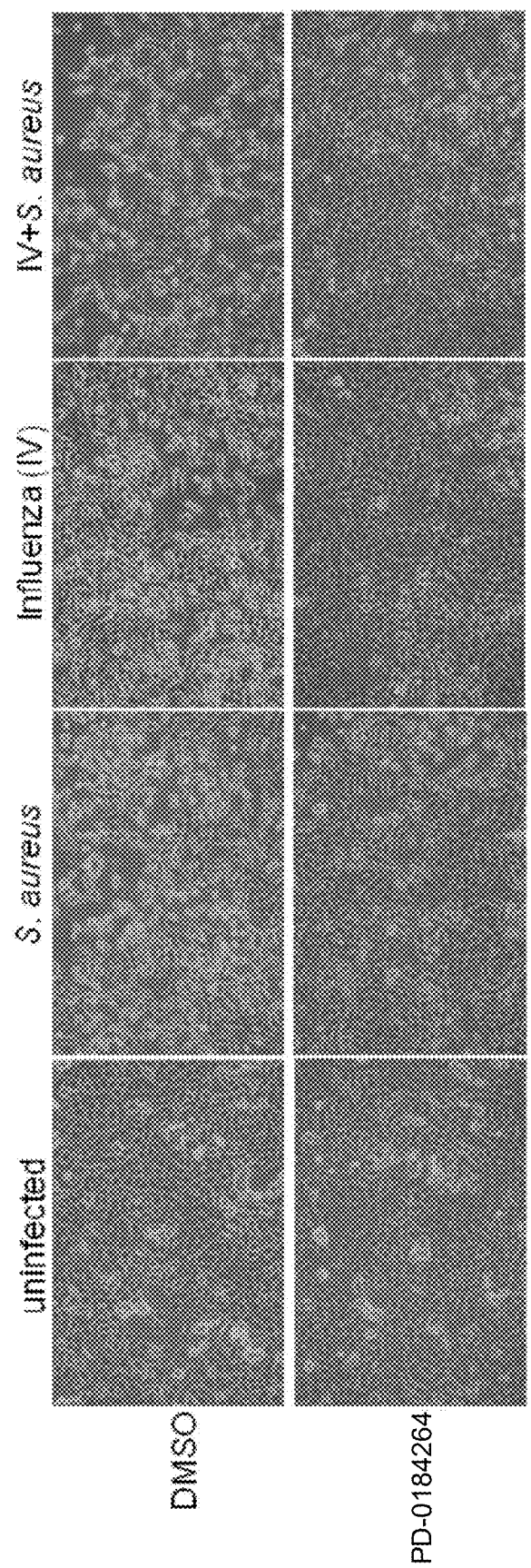
FIG. 13:
Pictures showing that treatment of cells with PD-0184264 strongly decreases the pathogen-induced CPE (cytopathic effect) upon singular bacterial (S. aureus) or viral (Influenza IV) infection and co-infection.

Influenza virus (IV) infection results in enhanced expression of antiviral cytokines, most importantly type I IFNs that activate critical downstream antiviral responses and may also potentiate subsequent bacterial infections. To see whether treatment with CI-1040 or PD-0184264 would sensitize cells for a secondary S. aureus infection, cell cultures of immortalized human alveolar basal epithelial cells (A549) were infected with influenza IV and S. aureus in the presence or absence of the inhibitors. Specifically, A549 cells were pre-treated for 1 h with 10 µM of the specific MEK-inhibitor PD-0184264 or DMSO as solvent control. Afterwards, cells were rinsed with PBS and infected with influenza virus (IV) (MOI as indicated) for 30 min at 37° C., 5% $CO_2$. Subsequently, cells were washed with PBS and infected with S. aureus 6850 (MOI as indicated) in the presence or absence of the inhibitor for 3 h. To avoid bacterial over-growth, an antibiotic wash step with lysostaphin (2 μg/mL) was performed for 20 min at 37° C. to remove not-internalized bacteria. Then, cells were washed once and were further incubated until 24 h p.i. in the presence of the inhibitor or solvent. At the end of the incubation period, the cell monolayer was analyzed via light microscopy. Microscopic examination revealed that superinfection with both pathogens resulted in a highly increased cytopathic effect (CPE) compared to singular infections (FIG. 13, upper panel). The CPE was completely abolished in presence of PD-0184264 (FIG. 13, lower panel) indicating reduced viral replication.

To see if treatment with PD-0184264 and with CI-1040 was comparable, A549 cells were pre-treated with 10 μM CI-1040, PD-0184264 or solvent (DMSO) for 60 min and then infected with influenza IV (H7N7) at a MOI of 0.001 at 37° C. The results are shown in FIGS. 14A and 14B, respectively. Alternatively, cells were left untreated (DMSO) and infected with IV (H1N1) at a MOI of 0.01 at 37° C. After 30 min the virus dilution was removed, cells were rinsed with PBS and supplemented with invasion medium with or without S. aureus 6850 (6850) (MOI 0.1) in the presence of 10 μM CI-1040, PD-0184264 or solvent control. 3 h post bacterial infection cells were treated with lysostaphin (2 μg/mL) for 20 min to remove extracellular bacteria. Cells were then washed and supplemented with infection medium containing the inhibitor or solvent. After a total incubation period of 24 h (post viral infection) intracellular bacterial titers were analyzed. Results represent means+SD of three individual experiments. Statistical significance was evaluated by one-way ANOVA followed by Tukey's multiple comparisons test (*$p<0.05$; $p<0.01$; *$p<0.001$; ****$p<0.0001$). As can be seen from FIG. 14A, treatment with CI-1040 did not sensitize cells for a secondary infection with S. aureus as no changes in intracellular bacterial load could be detected. Surprisingly, administration of PD-0184264 even resulted in reduced intracellular bacterial titers as can be seen from FIG. 14B. Comparable results were obtained when CI-1040 or PD-0184264 were administered at later times during on-going infection as shown in FIG. 14C.

To rule out that the reduction in viral and intracellular bacterial replication was a result of a cytotoxic effect of PD-0184264 on A549 cells, cell viability in presence of increasing concentrations was monitored for 24 and 48 hours. Additionally, a LDH-Assay was performed to determine membrane rupture due to inhibitor treatment. It was shown that treatment of A549 cells with PD-0184264 does not induce cell toxicity. A549 cells were treated for 24 (as shown in FIGS. 15A and C) or 48 (as shown in FIGS. 15B and D) hours with increasing concentrations of PD-0184264 (1, 5, 10, 20, 50 or 100 μM). After the incubation times, supernatants were taken for measurement of LDH release (shown in in FIGS. 15C, D) using the CytoSelect LDH Cytotoxicity Assay Kit according to the manufacturer's instructions. Additionally, viable cells were counted by staining with trypan blue. Cell viability was normalized to DMSO-treated cells and is shown as % viability. Data show means+SD of three independent experiments. Statistical significance was calculated by one-way ANOVA followed by Dunnett's multiple comparisons test (* $p<0.05$;  $p<0.01$; 27 * $p<0.001$).

Example 9: Determination of $IC_{50}$ Values for CI-1040 and PD-0184264

Inhibitor aliquots were dissolved in 100% DMSO (Master solution 10 mM). To analyze the IC50 values the following serial dilutions were prepared in a microtiter plate: 50 μM, 25 μM, 5 μM, 2.5 μM, 0.5 μM, 0.25 μM, 0.05 μM, 0.025 μM, 0.005 μM. 1 μl of each dilution was added to 49 μl of the kinase reaction mixture, yielding the following test concentrations: 1 μM, 500 nM, 100 nM, 50 nM, 10 nM, 5 nM, 1 nM, 0.5 nM, 0.1 nM.

3 μl active c-Raf1, 2 μl MEK1 wt und 3 μl ERK2wt of purified protein solutions were mixed with kinase buffer and 1 μl DMSO or DMSO/inhibitor (final volume 45 μl). The mixture was incubated for 30 min at room temperature in the dark. After this pre-incubation, ensuring inhibitor binding to the MEK protein, the kinase reaction was started by adding 5 μl of 10 mM ATP and mixing with the pipette. The samples were incubated for 30 min at 26° C. Thermo mixer (Eppendorf) at 500 rpm. To stop the kinase reaction, 5.5 μl of a 20% SDS solution was added and this mixture was subsequently incubated for 10 min at 50° C. Each sample was then diluted with 190 μl blocking buffer (1% BSA in TBST). 100 μl of each sample was added to the anti-ERK antibody coated wells of a 96-well-microtiter plate.

The kinase reaction samples (100 μl/well) were incubated for 60 min at room temperature in the anti-ERK antibody coated and BSA blocked wells of a 96-well microtiter plate. Plates were subsequently washed 3×5 min with 100 μl TBST washing buffer. To detect phosphorylated ERK, an anti phospho-ERK (p44/p42) antibody (1:3000, 100 μl/well in blocking buffer) was added and incubated overnight at 4° C.

After three washing steps (3×100 μl/well), a HRP-conjugated anti-mouse IgG specific antibody (1:1000 in TBST) was added and incubated for 60 min at room temperature. 100 μl/well of peroxidase substrate ABTS were added after three additional washing steps (3×100 μl/well TBST) and incubated for 30 min at 30° C. The substrate reaction was stopped by adding 2.5 μl of 20% SDS. The optical density (OD) of the mixture is measured at a wavelength of 405 nm in an ELISA-reader.

The cell free kinase assay revealed that 12.5-fold less CI-1040 (FIG. 16) is needed to inhibit 50% of the MEK activity compared to PD-0184264 that actually is a weaker inhibitor of MEK kinase. Thus, no one would have expected the strong antiviral and antibacterial effects of PD-0184264. However, as shown in the Examples before, PD-0184264 exhibits a stronger antiviral and antibacterial activity as compared to CI-1040 in vivo.

Example 10: Antiviral Activity of PD-0184264 in an In Vitro Assay

Drugs

CI-1040 [2-(2-chloro-4-iodophenylamino)-N-(cyclopropylmethoxy)-3,4-difluoro benzamide; Lot: CC-5395.0-16] and PD-0184264 (PD0184264) [2-(2-chloro-4-iodophenylamino)-N-3,4-difluoro benzoic acid; Lot: CC-5595.4-10] were synthesized at ChemCon GmbH (Freiburg, Germany). For cell culture experiments, a 10 mM stock solution of CI-1040 (M=478.66 g/mol) and PD-0184264 (M=409.55 g/mol) was prepared in DMSO (Merck-Millipore; Germany).

Virus and Cells

Virus inhibition experiments where conducted with influenza A virus strain RB1 [A/Regensburg/D6/09 (H1N1pdm09)] with an MOI of 0.001.

Progeny Virus Inhibition Assay

A549 cells were infected with RB1 for 30 min at 37° C. in a 5% $CO_2$ atmosphere. After incubation, the virus dilution was aspirated, and the cells were rinsed with PBS and supplemented with 500 μl IMDM (Iscove's Modified Dulbecco's Medium)/BA (Bovine Albumin)—Medium (0.2% BA, 1 mM $MgCl_2$, 0.9 mM $CaCl_2$, 100 U/ml penicillin, 0.1 mg/ml streptomycin) and 0.6 µl TPCK-treated Trypsin in presence of either 10 µM CI-1040 or different concentrations of PD-0184264 (100 µM, 50 µM, 10 µM, 5 µM, 1 µM, 0.5 µM and 0.1 µM, final DMSO concentration=1%) for 24 h at 37° C. in 5% $CO_2$. The solvent control was IMDM/BA-medium with 1% DMSO. The cell culture supernatants were collected to determine the progeny virus titers on MDCK II cells using the AVICEL® plaque assay, as described previously (Haasbach et al. 2011, Matrosovich et al. 2006).

WST-Assay

A549 cells were seeded in a 96-well flat-bottom tissue plate (Greiner, Germany) and were grown overnight. Thereafter, cells were treated with different concentrations of PD-0184264 (100 µM, 50 µM, 10 µM, 5 µM, 1 µM, 0.5 µM and 0.1 µM) dissolved in 100 µl IMDM (ThermoFisher, Germany) supplemented with 5% fetal calf serum (Sigma-Aldrich; Germany) final DMSO concentration=1% and cultivation was performed at 37° C. and 5% $CO_2$ for 24 h. Thereafter, 10 µl WST-1 reagent (Roche, Germany) was added to the culture medium and incubated for four hours. During this time, the stable tetrazolium salt WST-1 was cleaved to a soluble formazan by metabolically active cells in the culture. After this incubation period, the formazan dye formed was quantitated with ELISA reader at 405 nm. The measured absorbance directly correlated to the number of viable cells.

Results

Figure 17:
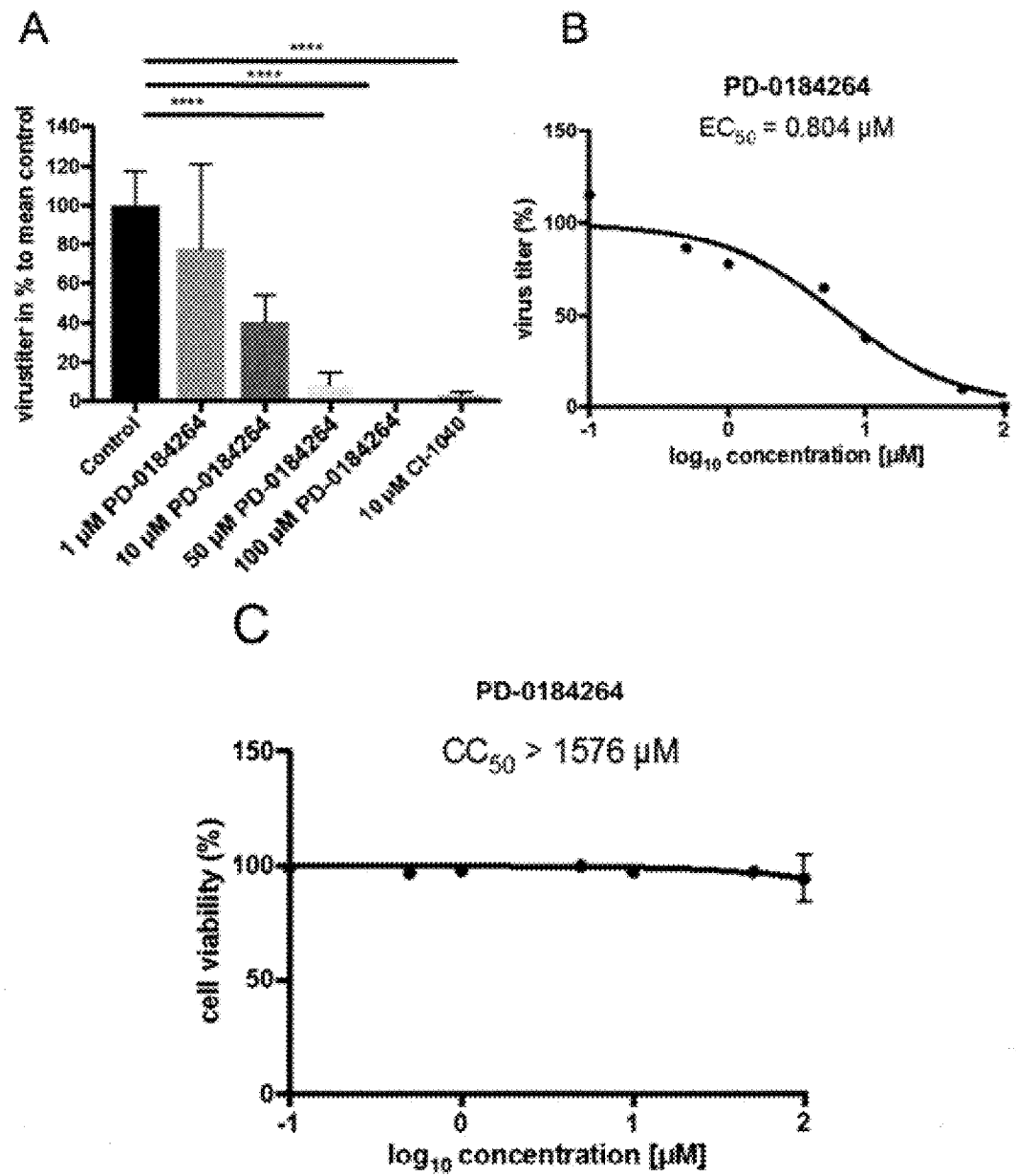
FIG. 17: Antiviral activity of PD-0184264 against influenza virus H1N1pdm09 in an in vitro assay.
(A) A549 cells were infected with virus (MOI=0.001) to determine virus titre reduction. (B) A549 cells were infected with virus RBI (MOI=0.001) and treated with different concentrations of PD-0184264 (100 µM, 50 µM, 10 µM, 5 µM, 1 µM, 0.5 µM and 0.1 µM) to determine the $EC_{50}$ value.
(C) A549 cells were treated with different concentrations of PD-0184264 (100 µM, 50 µM, 10 µM, 5 µM, 1 µM, 0.5 µM and 0.1 µM) for 24 h followed by four hours WST-staining to determine the $CC_{50}$ value.

The antiviral activity of PD-0184264 against RB1 was investigated in the standard virus inhibition assay (FIG. 17A). A 98.87±0.03% reduction of virus titer was found when cells were treated with 100 µM PD-0184264 (P>0.0001) was found. A similar reduction was found with 50 µM PD-0184264 (91.50±2.08%; P>0.0001). In contrast only a weak reduction of virus titer was found, when 10 µM PD-0184264 was used (58.97±4.45%). 1 µM PD-0184264 resulted in almost no reduction of progeny virus. Thus, in comparison to the virus reduction with 10 µM CI-1040 (96.78±0.65%; P>0.0001) an almost 10-fold higher concentration of PD-0184264 is needed to achieve similar reduction of progeny influenza virus. This is also in line with the EC50 value for PD-0184264 compared to CI-1040. For PD-0184264 the $EC_{50}$ value is 0.804 µM (FIG. 17B). In another work, the $EC_{50}$ value for CI-1040 against RB1 could be determined as 0.026 µM (Haasbach et al. 2017). The PD-0184264 $CC_{50}$ value of >1576 (FIG. 17C) is higher compared to CI-1040 (>312.3 µM; Haasbach et al. 2017). Thus, PD-0184264 has a S.I.=1960 (selectivity index).

Summary/Discussion

The results demonstrate a reduced antiviral activity of PD-0184264 in cell culture, i.e. in vitro, compared to CI-1040. Almost a 10-fold higher concentration of PD-0184264 is required to achieve the same virus reduction as with CI-1040 in an in vitro assay. The $EC_{50}$ value difference between these two compounds is even more pronounced. Here, the $EC_{50}$ value of PD-0184264 is 31-fold higher compared to the $EC_{50}$ value of CI-1040 (Haasbach et al. 2017). The S.I. of PD-0184264 against RB1 on A549 cells is also reduced compared to CI-1040 development.

Example 11: In Vivo Reduction of Virus Titer in the Lung of Mice by PD-0184264

(A) After H1N1pdm09 infection female C57BL/6 mice were treated with either 2.8, 8.4 or 25 mg/kg PD-0184264 (left side) or with 25, 75 or 150 mg/Kg CI-1400 (left side) the oral route. 24 hrs after infection the animals were killed and lung was taken to prepare a 10% suspension. Virus titer was determined using the standard method. Virus titer of mice treated with the two MEK-inhibitors were compared to virus titer of mice treated with solvent (Control) alone. Virus tier in the lungs of control mice was set to 100% (black bar). Graphpad Prism 7 software was used to illustrate both figures.

Drugs

CI-1040 [2-(2-chloro-4-iodophenylamino)-N-(cyclopropylmethoxy)-3,4-difluoro benzamide; Lot: CC-5395.0-16] and PD-0184264 (PD0184264) [2-(2-chloro-4-iodophenylamino)-N-3,4-difluoro benzoic acid; Lot: CC-5595.4-10] were synthesized at ChemCon GmbH (Freiburg, Germany).

For oral application of 25 mg/kg, 2.5 mg of PD-0184264 were dissolved in 50 µl DMSO (Sigma-Aldrich, Germany) and further diluted with 0.15 ml Cremophor EL (Merck-Millipore, Germany) and 0.8 ml PBS (Gibco, Germany). For application of 8.4 mg/kg and 2.8 mg/kg, 0.84 mg or 0.28 mg PD-0184264 were dissolved with 50 µl DMSO (Sigma-Aldrich, Germany) and further diluted with 0.15 ml Cremophor EL/0.8 ml PBS. 202.5 mg CI-1040 were dissolved in 0.5 ml DMSO/0.15 ml Cremophor EL/0.8 ml PBS and further diluted with Cremophor EL and PBS.

Animals

Eight week old female C57Bl/6 mice (Charles River Laboratories, Germany) with a body weight of 21.0-24.0 g at administration were used for antiviral studies. The animals were normally fed. Drinking water was available ad libitum.

Drug Application

Drugs were administrated using a single dosing on test day 1 by oral gavage. The application speed was 15 s per dose with an administration volume of 200 µl.

Lung Virus Titration Assay

Mice were sacrificed 24 h post infection and lungs were weighed, transferred into a Lysing Matrix D tube (MP Bio) and BSS was applied in an amount of the 10-fold volume of the lung. Organs were shredded using the FastPrep FP 120 (Savant). To remove the cell debris the homogenates were centrifuged for 15 min at 2000 rpm and the supernatant collected. The determination of virus titer in homogenates was performed using the AVICEL® plaque assay as described previously (Haasbach et al. 2011, Mastrosovich et al. 2006).

Summary/Discussion

FIG. 18 shows the results of the experiments. In comparison to the control experiment, only concentrations of 75 mg/kg or higher of CI-1040 showed any effect in reduction of virus titer. In contrast, PD-0184264 already showed a reduction of the virus titer in the lung at a concentration of 2.8 mg/kg to approx. 70%. At a concentration of 8.4 mg/kg, the virus titer is reduced to an amount of approx. 20%, whereas at 25 mg/kg the virus titer is reduced to approx. 10%. Thus, a 6-fold lower concentration of PD-0184264 is needed to achieve a similar effect as 150 mg/kg CI-1040 underlining the high potential of PD-0184264 for antiviral effects.

Example 12: PD-0184264 has a Higher Bioavailability Compared to CI-1040

(A) Male NMRI mice were treated with either 75 mg/kg CI-1040 (dark grey area) or with 75 mg/Kg PD-0184264 the intravenous route. Blood was collected at 15 min, 30 min, 1 h, 2 h, 4 h, 6 h, 8 h and 24 h (test day 2) after administration and plasma was analysed for the presence of the drug.

(B) Male NMRI mice were treated with either 150 mg/kg CI-1040 (dark grey area) or with 150 mg/Kg PD-0184264 per os using oral gavage. Blood was collected at 15 min, 30 min, 1 h, 2 h, 4 h, 6 h, 8 h and 24 h (test day 2) after administration and plasma was analysed for the presence of the drug. Each data point represents the mean value of three plasma samples. Graphpad Prism 7 software was used to illustrate both figures.

Drugs

CI-1040 [2-(2-chloro-4-iodophenylamino)-N-(cyclopropylmethoxy)-3,4-difluoro benzamide; Lot: CC-5395.0-15] and PD-0184264 (PD0184264) [2-(2-chloro-4-iodophenylamino)-N-3,4-difluoro benzoic acid; Lot: CC-5595.4-10] were synthesized at ChemCon GmbH (Freiburg, Germany). For i.v. application, 30.65 mg CI-1040 were dissolved in 0.075 ml DMSO (Sigma-Aldrich, Switzerland) and further diluted with 0.225 ml Cremophor EL (Merck-Millipore, Germany) and 2.7 ml PBS (Gibco, Germany). 34.88 mg PD-0184264 were dissolved in 0.075 ml DMSO and further diluted with 0.225 ml Cremophor EL/2.7 ml PBS. For oral application, 202.5 mg CI-1040 were dissolved in 0.5 ml DMSO/1.5 ml Cremophor EL/8.0 ml PBS. 81.0 mg PD-0184264 were dissolved in 0.2 ml DMSO/0.6 ml Cremophor EL/3.2 ml PBS.

Animals

Eight week old male NMRI mice (Charles River Laboratories, Germany) with a body weight of 23.9-36.5 g at administration were used for pharmacokinetic studies. The animals were normally fed. Drinking water was available ad libitum.

Blood Sampling and Preparation of Plasma

Experiments were performed at LPT GmbH (Hamburg, Germany). Sufficient whole blood—taken under isoflurane anaesthesia—was collected to obtain at least 2×100 µL Li-Heparin plasma of 3 animals per group and time-point at the following times: 0 (predose), 15 min, 30 min, 1 h, 2 h, 4 h, 6 h, 8 h and 24 h (test day 2) after administration. The whole blood samples were instantly cooled using an Iso-Therm-Rack system (Eppendorf AG, Germany) until centrifugation within 0.5 hours after withdrawal. Immediately after centrifugation, the samples were stored at −20° C. until further analysis. Plasma analysis was performed using standard procedures at Prolytic GmbH (Frankfurt, Germany).

Drug Application

Drugs were either administered using a single dosing on test day 1 by oral gavage or by Intravenous bolus injection into a tail vein. The Injection speed was 15 s/dose with an administration volume of 200 µl.

Results

The pharmacokinetic experiments revealed that a higher exposure of PD-0184264 was found after i.v. (FIG. 19A) and by per os (FIG. 19B) application in the plasma of mice compared to CI-1040 with AUC values of 1953.68 µg*h/ml PD-0184264, which are much higher than the values for CI-1040. Note that at eight hours after i.v. application and after by per os application of CI-1040 almost no drug was detected in the plasma. In contrast, after per os application of PD-0184264 2 at the 8 h data point still a high concentration was found.

Summary/Discussion

The drastic difference in the plasma exposure for PD-0184264 and CI-1040 after single i.v. application already gives rise to the assumption that CI-1040 might degrade rapidly. The inventors assumed that the drug declines in a mono-exponential fashion. In general, this assumption is valid. At low concentrations, drug usually declines in mono-exponential fashion. And the terminal elimination rate constant does not change over time or with different concentrations of circulating drug. Nevertheless, at this point we don't know whether other processes such as an enterohepatic circle play a significant role in the terminal phase of the pharmacokinetic profile.

Taken together, PD-0184264 shows a high antiviral activity than CI-1040 in vivo, which may be based on the higher bioavailability of the drug.

Example 13: PD-0184264 has an Enlarged Treatment Window

Drug and Drug Application

For oral application of 25 mg/Kg 10 mg of PD-0184264 were dissolved in 50 µl DMSO (Sigma-Aldrich, Germany) and further diluted with 0.15 ml Cremophor EL (Merck-Millipore, Germany) and 0.8 ml PBS (Gibco, Germany). For application of solvent 50 µl DMSO (Sigma-Aldrich, Germany) was diluted with 0.15 ml Cremophor EL (Merck-Millipore, Germany) and 0.8 ml PBS (Gibco, Germany). Drugs were administered using a twice daily (BID) dosing by oral gavage with a time gap of eight hours. Treatment started either 24, 48 or 72 hours after infection. The application speed was 15 sec/dose with an administration volume of 50 µl.

Animals

Eight week old female C57Bl/6 mice (Charles River Laboratories, Germany) with a body weight of 17.0-21.0 g at administration were used for the survival studies. The animals were normally fed. Drinking water was available ad libitum.

Virus Infection

For infection, the animals were anesthetized by intraperitoneal injection of 200 µl ketamine/rompun. Equal amounts of a 2% rompun (Bayer) and a 10% ketamine (Sanofi) stock solution were mixed at a ratio of 1:10 with PBS. Mice were infected intranasally with $3\times10^5$ pfu of strain A/Regensburg/D6/2009 Influenza H1N1pdm09 (5×MLD50). Adequate virus doses were diluted in 50 µl BSS and 25 µl were inoculated into each nostril. All animal studies were approved by the Institutional Animal Care and Use Committee of Tuebingen.

Clinical Observation

According to the rules of the regulatory authorities, the animals were observed and weighed daily. Prior to onset of clinical symptoms mice were observed twice daily and three times daily after onset of disease. The mice had to be sacrificed, when a 20% reduction of the bodyweight was found. None of the animals died in the cage, all were sacrificed by $CO_2$ treatment followed by neck dislocation.

Results

Female C57BL/6 mice were infected with H1N1pdm09. Treatment with 25 mg/kg PD-0184264 started either 24, 48 or 72 hours after infection. Mice that functioned as controls received the solvent alone. These animals had to be sacrificed between days four—eight after infection, because they showed a bodyweight reduction of ≥20%. When treatment started 24 hours after infection two out of eight animals had to be sacrificed at day ten, while six out of eight mice were protected. There was no difference in bodyweight reduction, nevertheless at day ten after infection the mice gained weight again until the end of the observation period. The difference between solvent and PD-0184264 treated mice regarding survival was statistically significant (Log-rank Mantel-Cox test P=0.0001). When treatment started 48 hours after infection three out of eight animals had to be sacrificed between days eight and ten and five out of eight mice were protected. Again, there was no difference in bodyweight reduction. At day 9 after infection the mice gained weight again until the end of the observation period. The difference in survival again was significant (Log-rank Mantel-Cox test P=0.0004). The difference in survival was also significant (Logrank Mantel-Cox test P=0.0002) even treatment started as late as 72 hours after infection. Here, six out of eight animals had to be sacrificed between days seven and ten, while two out of eight mice were protected. Beginning at day nine after infection, mice increased their bodyweight.

Summary/Discussion 25 mg/kg PD-0184264 treatment of H1N1pdm09 infected mice leads to a significant difference in survival, even though the drug was administered as late as 72 hours after infection.

Example 14: Phase I Clinical Trials on PD-0184264 in Healthy Human Subjects

A randomized, double blind, placebo-controlled dose escalation study was conducted and demonstrated the safety and tolerability of PD-0184264 in 70 healthy volunteers. It followed an adaptive design with a starting dose of 100 mg and up to three escalation steps in seven arms, following a single ascending dose/multiple ascending dose (SAD/MAD) regime. Administration scheme was one dose PD-0184264, escalating 100 mg to 900 mg (SAD), followed by seven doses PD-0184264, escalating 100 mg to 600 mg QD over seven days (MAD). Each dose cohort was considered to be safe by the Safety Review Committee (SRC), with release allowed for the next higher dose (up to SAD 900 mg and MAD 600 mg, respectively). The observed pharmacokinetic profile supports the intended once-daily regime for the further clinical development.

Only few adverse events in total and no serious adverse events were observed during the trial. PD-0184264 is thus considered to be safe and well tolerable. Pharmacokinetics exposure and determination of MEK inhibition were verified and confirm the maintenance of clinically relevant blood levels.

REFERENCES

Bright, R. A., Shay, D. K., Shu, B., Cox, N J. and Klimov, A. I. (2006). Adamantane resistance among influenza A viruses isolated early during the 2005-2006 influenza season in the United States. JAMA: The Journal of the American Medical Association 295, 891-894

Chertow, D. S. and Memoli, M. J. (2013). Bacterial coinfection in influenza: a grand rounds review. JAMA: The Journal of the American Medical Association 309, 275-282.

De Clercq, E. and Neyts, J. (2007). Avian influenza A (H5N1) infection: targets and strategies for chemotherapeutic intervention. Trends in pharmacological sciences 28, 280-285.

Gillet, Y., Vanhems, P., Lina, G., Bes, M., Vandenesch, F., Floret, D. and Etienne, J. (2007). Factors predicting mortality in necrotizing community acquired pneumonia caused by Staphylococcus aureus containing Panton-Valentine leukocidin. Clinical infectious diseases: an official publication of the Infectious Diseases Society of America 45, 315-321.

Grundmann, H., Aires-de-Sousa, M., Boyce, J. and Tiemersma, E. (2006). Emergence and resurgence of methicillin-resistant Staphylococcus aureus as a public-health threat. Lancet 368, 874-885.

Haasbach, E. et al (2017). The MEK-inhibitor CI-1040 displays a broad anti-influenza virus activity in vitro and provides a prolonged treatment window compared to standard of care in vivo. Antiviral research 142, 178-184.

Hayden, F. G. and Hay, A. J. (1992). Emergence and transmission of influenza A viruses resistant to amantadine and rimantadine. Current topics in microbiology and immunology 176, 119-130.

Hrincius, E. et al. (2010): CRK adaptor protein expression is required for efficient replication of avian influenza A viruses and controls JNK mediated apoptotic responses. Cellular microbiology 12, 831-843

Iwao, Y., Ishii, R., Tomita, Y., Shibuya, Y., Takano, T., Hung, W. C., et al. (2012). The emerging ST8 methicillin-resistant Staphylococcus aureus clone in the community in Japan: associated infections, genetic diversity, and comparative genomics. J Infect Chemother 18, 228-240.

LoRusso, P., Adjei, A., Varterasian, M., Gadgeel, S., Reid, J., Mitchell, D., et al. (2005). Phase I and Pharmacodynamic Study of the Oral MEK Inhibitor CI-1040 in Patients With Advanced Malignancies. Journal of Clinical Oncology 23(23), 5281-5293.

Ludwig, S. (2009). Targeting cell signaling pathways to fight the flu: towards a paradigm change in anti-influenza therapy. Journal of Antimicrobial Chemotherapy, 64, 1-4.

Mackey, T. K., Liang, B. A., 2012. Lessons from SARS and H1N1/A: employing a WHO-WTO forum to promote optimal economic-public health pandemic response. J Public Health Policy 33, 119-130.

Matrosovich M, Matrosovich T, Garten W, Klenk H D (2006). New low-viscosity overlay medium for viral plaque assays. Virol J. 3:63.

Miller, M., Donat, S., Rakette, S., Stehle, T., Kouwen, T. R., Diks, S. H., Dreisbach, A., Reilman, E., Gronau, K., Becher, D., Peppelenbosch, M. P., van Dijl, J. M., Ohlsen, K. (2010). Staphylococcal PknB as the first prokaryotic representative of the proline-directed kinases. PLoS One, 5, e9057

Monto, A. S., Black, S., Plotkin, S. A., Orenstein, W. A., 2011. Response to the 2009 pandemic: effect on influenza control in wealthy and poor countries. Vaccine 29, 6427-6431.

Moran, G. J., Krishnadasan, A., Gorwitz, R. J., Fosheim, G. E., McDougal, L. K., Carey, R. B., et al. (2006). Methicillin-resistant S. aureus infections among patients in the emergency department. The New England Journal of medicine 355, 666-674.

Morens, D. M., Taubenberger, J. K. and Fauci, A. S. (2008). Predominant role of bacterial pneumonia as a cause of death in pandemic influenza: implications for pandemic influenza preparedness. The Journal of infectious diseases 198, 962-970.

Moss, R. B., Davey, R. T., Steigbigel, R. T., Fang, F., 2010. Targeting pandemic influenza: a primer on influenza antivirals and drug resistance. J Antimicrob Chemother 65, 1086-1093.

Neumann, G., Noda, T. and Kawaoka, Y. (2009). Emergence and pandemic potential of swine-origin H1N1 influenza virus. Nature 459, 931-939.

Paddock, C. D., Liu, L., Denison, A. M., Bartlett, J. H., Holman, R. C., Deleon-Carnes, M., et al. (2012). Myocardial injury and bacterial pneumonia contribute to the pathogenesis of fatal Influenza B Virus infection. The Journal of infectious diseases 205, 895-905.

Parker, D. and Prince, A. (2012). Immunopathogenesis of *Staphylococcus aureus* pulmonary infection. Seminars in immunopathology 34, 281-297.
Parry, J. (2013). H7N9 avian flu infects humans for the first time. Bmj 346, f2151.
Pinto, L. H. and Lamb, R. A. (2006). The M2 proton channels of influenza A and B viruses. The Journal of biological chemistry 281, 8997-9000.
Pinto, L H. and Lamb, R. A. (2007). Controlling influenza virus replication by inhibiting its proton channel. Molecular bioSystems 3, 18-23.
Pleschka, S., Wolff, T., Ehrhardt, C., Hobom, G., Planz, O., Rapp, U. R., Ludwig, S., 2001. Influenza virus propagation is impaired by inhibition of the Raf/MEK/ERK signalling cascade. Nat Cell Biol 3, 301-305.
Rakette, S., Donat, S., Ohlsen, K and Stehle, T (2012). Structural analysis of *Staphylococcus aureus* serine/threonine kinase PknB. PLoS One 7(6), e39136.
Robertson, J. S., Inglis, S. C., 2011. Prospects for controlling future pandemics of influenza. Virus Res 162, 39-46.
Shilo, N. and Quach, C. (2011). Pulmonary infections and community associated methicillin resistant *Staphylococcus aureus*: a dangerous mix? Paediatric respiratory reviews 12, 182-189.
Tamber, S., Schwartzman, J. and Cheung, A. L. (2010). Role of PknB kinase in antibiotic resistance and virulence in community-acquired methicillin-resistant *Staphylococcus aureus* strain USA300. Infection and Immunity 78, 3637-3646.
Taubenberger, J. K, and Kash, J. C. (2010). Influenza virus evolution, host adaptation, and pandemic formation. Cell host & microbe 7, 440-451.
Wabnitz, A., Mitchell, D, and Wabnitz, D. (2004). In Vitro and in Vivo Metabolism of the Anti-Cancer Agent CI-1040, a MEK Inhibitor, in Rat, Monkey, and Human. Pharmaceutical Research 21(9), 1670-1679.
Tuchscherr, L. et al. (2011). *Staphylococcus aureus* phenotype switching: an effective bacterial strategy to escape host immune response and establish a chronic infection. EMBO molecular medicine 3, 129-141

The invention claimed is:

1. A method of treatment of a viral disease comprising administering to a subject in need thereof an effective amount of PD-0184264 or a pharmaceutically acceptable salt thereof, wherein the subject has been symptomatic for the viral infection for at least 24 hours when treatment is started.

2. The method of claim 1, wherein the subject has been symptomatic for the viral infection for at least 36, at least 48 hours, or at least 72 hours when treatment is started.

3. The method of claim 1 which further prevents or treats a bacterial co-infection.

4. The method of claim 1, wherein the viral infection is a respiratory tract infection caused by a negative or positive strand RNA virus.

5. The method of claim 4, wherein the negative strand RNA virus is an influenza virus.

6. The method of claim 5, wherein the virus is influenza A virus or influenza B virus.

7. The method of claim 6, wherein the influenza A virus is selected from the group consisting according to H1N1, H2N2, H3N2, H5N6, H5N8, H6N1, H7N2, H7N7, H7N9, H9N2, H10N7, N10N8 or H5N1.

8. The method of claim 6, wherein the Influenza B virus is selected from the group consisting of IBV-type Yamagata or Victoria.

9. The method of claim 1, wherein the viral infection is caused by a positive strand RNA virus.

10. The method of claim 9, wherein the virus is a coronavirus.

11. The method of claim 10, wherein the virus is SARS-COV, SARS-CoV2, or MERS.

12. The method of claim 1, wherein the virus is resistant to standard antiviral treatment.

13. The method of claim 12, wherein the standard antiviral treatment is administration of oseltamivir, zanamivir, peramivir, amantadine, rimantadine, favipiravir, baloxavir marboxil and/or pimodivir.

14. The method of claim 12, wherein the virus is H1N1 virus A H275Y mutant.

15. The method of claim 1, wherein the subject has been treated with a standard antiviral prior to administration of PD-0184264.

16. The method of claim 1, wherein PD-0184264 or a pharmaceutically acceptable salt thereof is administered in combination with a neuraminidase inhibitor or a pharmaceutically acceptable salt thereof, wherein the neuraminidase inhibitor is selected from oseltamivir, oseltamivir phosphate, zanamivir, laninamivir or peramivir or a pharmaceutically acceptable salt thereof.

17. The method according to claim 1, wherein the subject is a vertebrate.

18. The method of claim 1, wherein PD-0184264 is administered to a human subject once daily in a dose of 100 to 900 mg.

19. The method according to claim 1, wherein the subject is a human.

20. The method of claim 1, wherein PD-0184264 is administered to a human subject once daily in a dose of 600 mg.

21. The method of claim 1, wherein PD-0184264 is administered to a human subject on 1 to 21 consecutive days.

22. The method of claim 1, wherein PD-0184264 is administered to a human subject on 7 to 14 consecutive days.

23. The method of claim 1, wherein PD-0184264 is administered to a human subject in an oral dosage form.

* * * * *